United States Patent [19]
Lollo et al.

[11] Patent Number: 5,994,316
[45] Date of Patent: Nov. 30, 1999

[54] METHOD OF PREPARING POLYNUCLEOTIDE-CARRIER COMPLEXES FOR DELIVERY TO CELLS

[75] Inventors: Charles P. Lollo, Encinitas; Todd C. Mockler; Deborah Y. Kwoh, both of Carlsbad, all of Calif.

[73] Assignee: The Immune Response Corporation, Carlsbad, Calif.

[21] Appl. No.: 08/604,306

[22] Filed: Feb. 21, 1996

[51] Int. Cl.$^6$ ................................................ A61K 48/00
[52] U.S. Cl. .................................... 514/44; 935/52
[58] Field of Search ................ 435/172.3; 514/44; 530/395, 324; 525/54.1; 536/23.1; 935/52

[56] References Cited

U.S. PATENT DOCUMENTS

| | | | |
|---|---|---|---|
| 4,847,240 | 7/1989 | Ryser et al. | 514/12 |
| 5,166,320 | 11/1992 | Wu et al. | 530/395 |

FOREIGN PATENT DOCUMENTS

| | | |
|---|---|---|
| WO 9422485 | 10/1994 | WIPO . |
| WO 95/25809 | 9/1995 | WIPO . |
| WO 9611712 | 4/1996 | WIPO . |

OTHER PUBLICATIONS

Wu et al., (1987), "Receptor–Mediated In Vitro Gene Transformation By A Soluble DNA Carrier System", *The Journ. of Biol. Chem.* 262:4429–4432.

Wu et al., (1988), "Receptor–Mediated Gene Delivery And Expression In Vivo", *The Journ. of Biol. Chem.* 263:14621–14624.

Wu et al., (1989), "Targeting Genes Delivery And Persistent Expression Of A Foreign Gene Driven By Mammalian Regulatory Elements In Vivo", *The Journ. of Biol. Chem.* 264:16985–16987.

Wu et al., (1991), "Delivery Systems For Gene Therapy", *Biotherapy 3*: 87–95.

Cotten et al., (1990) *PNAS* 87:4033–4037.

Wagner et al., (1991) *PNAS* 88:4255–4259.

Perales et al., (1994) *PNAS* 91:4086–4090.

Boussif et al., (1995) *PNAS* (*Biochemistry*) 92:7297–7301.

Branchereau, S. et al. (1994) "Factors Influencing Retroviral–Mediated Gene Transfer Info Hepatocytes In Vivo", *Human Gene Therapy* 5:803–808.

Dai, Y. et al. (1995) "Cellular And Humoral Immune Response . . . Long–Term Expression", *Proc. Natl. Acad. Sci. USA* 92:1401–1405.

Ferkol, T. et al. (1993) "Regulation Of The Phosphoenolpynuvate . . . Receptor–Mediated Gene Transfer", *Faseb J7* 7:1081–1091.

Gao, L. et al. (1993) "Direct In Vivo/Gene Transfer To Airway . . . Adenovirus–Polylysine–DNA Complexes", *Hum. Gene Ther.* 4:17–24.

Guy et al. (1995) *Molecular Biotechnology* 3:237–248.

Hickman, M.A. et al. (1994) "Gene Expression Following Direct Injection Of DNA Into Liver", *Hum. Gene Ther.* 5:1477–1483.

Kabanov, A.V. et al. (1991) "DNA Interpolyelectrolyte Complexes . . . Efficient Cell Transformation", *Biopolymers* 31:1437–1443.

Kabanov, A.V. et al. (1984) "Soluble Interpolymeric Complexes . . . Synthetic Polyelectrolytes", *Pure Appl. Chem.* 56:343–354.

Kabanov, A.V. et al. (1993) "Efficient Transformation Of Mammalian Cells Using DNA . . . Carbon Chain Polycations", *Bioconjug. Chem.* 4:448–454.

Kabonov, A.V. et al. (1995) "DNA Complexes With Polycations For The Delivery Of Genetic Material Into Cells", *Bioconjug. Chem.* 6:7–20.

Ledley, F.D. et al. (1995) "The Promise Of Genes As Pharmaceutical Products", *Human Gene Therapy* 6:1129–1144.

Liu, Y. et al. (1995) "Cationic Liposome–Medicated Intraveneous Gene Delivery", *J. of Bio. Chem.* 270:24864–24870.

McKee, T.D. et al., (1994) "Preparation Of Asialoorosomucoid–Polylysine Conjugates", *Bioconjug. Chem.* 5:306–311.

Merwin, J.R. et al. (1994) "Targeted Delivery Of DNA Using YEE . . . Asialoglycoprotein Receptor", *Bioconjug. Chem.* 5:612.

Midoux, P. et al. (1993) "Specific Gene Transfer Mediated . . . Hepatoma Cells", *Nucl. Acids. Res.* 21:871–878.

Nishida, K. et al. (1991) "Hepatic Disposition Characteristics Of Electrically . . . In Vivo And In The Perfused Liver", *Pharm. Research* 8:437–444.

Strass, M. (1994) "Liver–Directed Gene Therapy: Prospects And Proglems", *Gene Therapy* 1:156–164.

Thierry, A.R. et al., (1995) "Systemic Gene Therapy: Biodistribution And Long–Term Expression Of A Transfene In Mice", *Proc. Nat'l. Acad. Sci. USA* 92:9742–9746.

Uchida, Y. et al., (1977) "Distribution Of Neuraminidase In Arthobacter . . . Affinity Chromatography", *J. Biochem.* 82:1425–1433.

Warren, L. (1959) "The Thiobarbituric Acid Assay Of Sialic Acids" *J. Biol. Chem.*, 234:1971–1975.

Weinhues et al. (1987) *DNA* 6:81–89.

Wilson, J. M. et al. (1992) Hepatocyte–Directed Gene Transfer In Vivo Leads To Transient . . . Receptor–Devicient Rabbvits, *J. Biol. Chem.*267:963–967.

Wagner, E. et al., "Transferrin–polycation conjugates as carriers for DNA uptake into cells", *PNAS*, vol. 87, pp. 3410–3414 (1990).

Zenke, M. et al., "Receptor–mediated endocytosis of transferrin–polycation conjugates: An efficient way to introduce DNA into hematopoietic cells", *PNAS*, vol. 87, pp. 3655–3659 (1990).

*Primary Examiner*—Bruce R. Campbell
*Attorney, Agent, or Firm*—Lahive & Cockfield, LLP; Jane E. Remillard

[57] ABSTRACT

An improved method of forming substantially disperse and homogeneous polynucleotide-carrier complexes is disclosed. The polynucleotide-carrier complexes can be administered in vivo to obtain significant levels and duration of gene expression.

28 Claims, 15 Drawing Sheets

Fractions from 5-30% Optiprep Gradients run on AsOR-4K PL-pCMV-hGH complexes
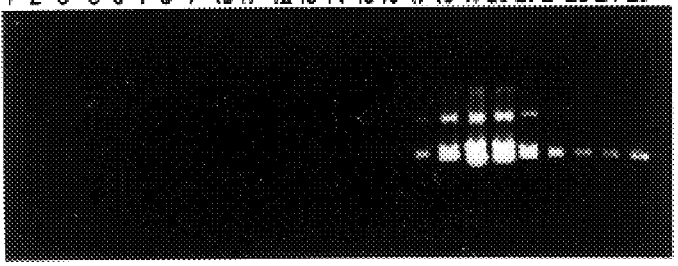
Free pCMV-hGH
89% complexed
AsOR-4K PL-pCMV-hGH
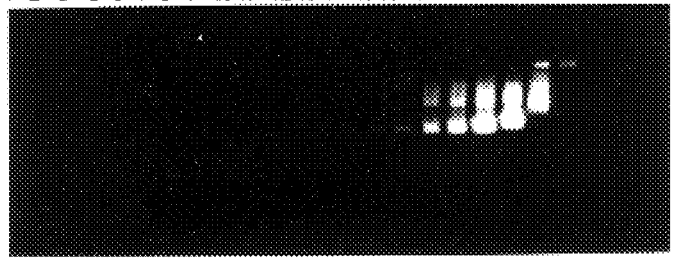
178% complexed
AsOR-4K PL-pCMV-hGH
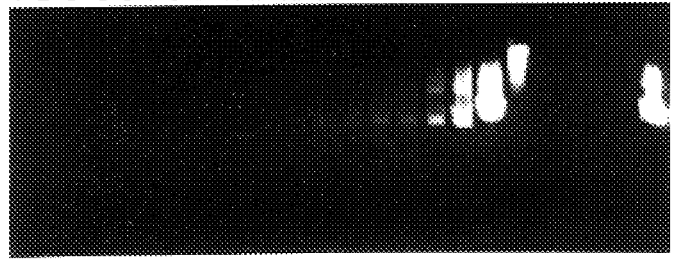
356% complexed
AsOR-4K PL-pCMV-hGH
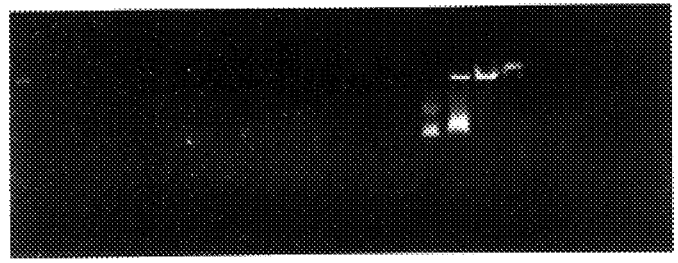
890% complexed
AsOR-4K PL-pCMV-hGH
Fig. 12

METHOD OF PREPARING POLYNUCLEOTIDE-CARRIER COMPLEXES FOR DELIVERY TO CELLS

BACKGROUND OF THE INVENTION

A broad variety of therapeutic polynucleotides have been delivered to cells by receptor-mediated endocytosis. When linked to a target cell-specific ligand, the polynucleotide is cointernalized by the target cell along with the ligand. Once inside the cell, the polynucleotide is released in functional form, for example, as an expressible gene or as an antisense construct which inhibits expression of an endogenous gene. In the case of plasmid DNA, the plasmid is maintained in the target cell as a non-replicating episome without integrating into the cell's genome (Wilson et al. (1992) *J. Biol. Chem* 267(16):11483–11489).

The first report of receptor-mediated gene transfer resulting in detectable expression of the gene was by Wu et al. (1987) *J. Biol. Chem.* 262: 4429–4432. Wu et al. developed a novel system for delivering polynucleotides to cells based on their work involving the introduction of genes into hepatocytes via the asialoglycoprotein receptor (see also, Wu et al. (1988) *J. Biol. Chem.* 263: 14621–14624; Wu et al. (1989) *J. Biol. Chem.* 264: 16985–16987; Wu et al. (1991) *J. Biol. Chem.* 266: 14338–14342; U.S Pat. No. 5,166,320).

The system developed by Wu et al. employs a soluble polynucleotide-carrier complex made up of a gene or other polynucleotide electrostatically linked to a bifunctional carrier molecule. The carrier molecule, comprised of a polycation-ligand conjugate, serves the dual function of linking the gene (via the polycation moiety, e.g., polylysine) and binding to the target cell (via the ligand, e.g., an asialoglycoprotein), resulting in internalization of the carrier molecule by the cell.

To form the molecular complex, Wu et al. linked the gene to the carrier in a step-down dialysis from a high salt solution of approximately 2.0–3.0 M NaCl down to approximately 0.15 M, thereby slowly complexing the negatively charged DNA and the positively charged polycation-ligand carrier. Wu et al. recognized that the method used to form the complex must result in a structure which (a) is soluble in solution so that it can easily pass through physiological barriers when administered in vivo to reach target cells or tissues, (b) is stable extracellularly so that the polynucleotide remains linked to the carrier, and (c) releases the polynucleotide in functional form under intracellular conditions.

The polynucleotide delivery system developed by Wu et al. has since been used by several others to deliver a broad variety of genes to selected cells (see e.g., Chen et al. (1994) *Human Gene Therapy* 5:429–435; Ferkol et al. (1993) *FASEB* 7: 1081–1091; Midoux et al. (1993) *Nucleic Acids Research* 21(4):871–878; Martinez-Fong (1994) *Hepatology* 20(6):1602–1608; Plank et al. (1992) *Bioconjugate Chem.* 3:533–539; Wagner et al. (1990) *PNAS* 87:3410–3414; Chen et al. (1994) *FEBS Letters* 338:167–169; Ferkol et al. (1993) *J. Clin. Invest.* 92:2394–2400; Rojanasakul et al. (1994) *Pharmaceutical Res.* 11(12):1731–1736; and Ross et al. (1995) *Human Gene Therapy* 6:31–40). However, during this time, some variations on the method of forming the DNA complex have been made in an effort to increase the level and duration of expression obtained from the targeted gene.

For example, Cotten et al. (1990) *PNAS* 87: 4033–4037 and Wagner et al. (1991) *PNAS* 88: 4255–4259 formed polynucleotide-carrier complexes containing plasmid DNA linked to a transferrin-polycation carrier molecule. In contrast to the step-down dialysis method employed by Wu et al., Cotten et al. and Wagner et al. directly mixed the transferrinpolycation conjugate and the plasmid DNA, with and without additional free polycation, at a concentration of 0.15 M NaCl. Wagner et al. recognized that the polycation not only served to link the DNA, but also functioned to condense the DNA into small toroid structures of approximately 80–100 nanometers in diameter, facilitating its uptake by cells.

Perales et al. (1994) *PNAS* 91: 4086–4090 also modified Wu's system for forming polynucleotide-carrier complexes, with the goal of condensing the DNA to form highly compacted complexes which are easily taken into endosomes. Specifically, Perales et al. linked a plasmid encoding human factor IX to galactosylated polylysine by titration with increasing concentrations of NaCl, resulting in complexes of approximately 10–12 nanometers in diameter as measured by electron microscopy (see also, WO 95/25809).

In contrast to the step-down dialysis method of Wu et al. and the direct mixing method of Wagner et al., Perales et al. slowly added the carrier dropwise to a solution of the plasmid, both at 0.7 M NaCl, over the course of 30 minutes to one hour. This step resulted in a turbid, aggregated solution which was then slowly titrated with 3 μl aliquots (allowing at least 30 seconds between the addition of each new aliquot) of 5 M NaCl until a clear, unaggregated solution was obtained at a "critical" concentration of NaCl, somewhere between 0.97 M NaCl and 1.03 M NaCl. Further 2 μl aliquots of 5 M NaCl were then gradually added if a precipitate formed. The authors observed that when increasing the ionic strength of the mixture above the critical salt concentration, the DNA complexes assumed a non-functional rod-like conformation of increased diameter. They therefore conclude that the concentration of NaCl must be kept at or near the critical range, generally between 0.5 M and 1.5 M (roughly 3.5 to 10 times physiological levels) (see WO 95/25809 at page 35, lines 10–11).

There remains a need for a more practical method of forming high performance polynucleotide-carrier complexes which produce persistent and high levels of gene expression when delivered to cells both in vitro and in vivo.

SUMMARY OF THE INVENTION

The present invention pertains to a substantially disperse and homogeneous composition of polynucleotide-carrier complexes, and to a method of forming the same. The composition of polynucleotide-carrier complexes is formed by preparing a solution of cationic carrier molecules which contains a sufficient amount of a charge shielding agent to diminish aggregation of the carrier molecules. The charge shielding agent can be any compound capable of diminishing aggregation of cationic species which occurs in the absence of the charge shielding agent. The carrier solution is then combined with a polynucleotide at an optimal charge neutralization ratio for the particular carrier and polynucleotide being used (e.g., ranging from about 10–1000%, about 50–500%, or about 75–250%) to form a solution of polynucleotide-carrier complexes.

In one embodiment, the charge shielding agent is a salt, such as sodium chloride (NaCl), which is present in the carrier solution, prior to adding the polynucleotide, at a concentration of about 1.0–5.0 M, preferably about 4.0 to 5.0 M, more preferably about 4.7 M. The polynucleotide is combined with the carrier solution at a concentration which, when mixed with the carrier solution, results in a final salt concentration which does not substantially denature (e.g., affect the form) or inhibit the function of the polynucleotide, e.g., about 0.15–0.5 M, preferably about 0.3 M, yet which still maintains dispersity of the polynucleotide-carrier complexes.

In another embodiment of the invention, the cationic carrier solution further comprises a charge neutralizing agent in an amount sufficient to neutralize a portion (e.g., less than 50%, e.g., about 5 to 20%) of the positive charge of the carrier. A preferred charge neutralizing agent is a base, e.g., sodium hydroxide (NaOH), which is added to the carrier solution prior to adding the polynucleotide to a concentration of about 10–100 mM, preferably about 59 mM. The polynucleotide is combined with the carrier solution at a concentration which, when mixed with the carrier solution, results in a final concentration of charge shielding agent (e.g., salt) and charge neutralizing agent (e.g., base) which does not substantially denature (e.g., affect the form) or inhibit the function of the polynucleotide. When the charge shielding agent is a salt and the charge neutralizing agent is a base, the polynucleotide is combined with the carrier solution to a final salt concentration of about 0.15–0.5 M, preferably about 0.3 M, and a final base concentration of about 1.0–4.0 mM, preferably about 2.0 mM.

In another embodiment of the invention, the polynucleotide-carrier complexes are extruded through a filter (e.g., 50 nM) prior to being administered to cells.

A further aspect of the present invention provides a composition of substantially disperse and homogeneous polynucleotide carrier molecules formed by the method summarized above.

Another aspect of the invention provides a method of forming a substantially disperse and homogeneous composition of cationic carrier molecules.

Another aspect of the present invention provides a method for diminishing aggregation of cationic carrier molecules.

The disperse and homogenous polynucleotide-carrier complexes formed by the above summarized methods can be used to deliver a variety of polynucleotides to selected cells either in vivo or in vitro. Specifically, the polynucleotide-carrier complexes formed by the methods of the present invention can be used in methods of gene transfer to obtain high levels and duration of expression of transfected genes.

BRIEF DESCRIPTION OF THE FIGURES

FIG. 12 shows agarose gels of sucrose density gradient fractions containing the polynucleotide-carrier complexes described in FIG. 11.

DETAILED DESCRIPTION OF THE INVENTION

Figure 1A:
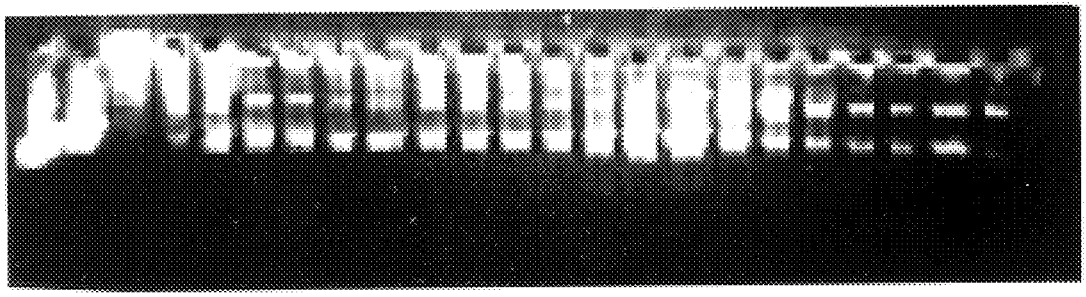
FIGS. 1A-1B show a comparison of agarose gels of sucrose density gradient fractions containing polynucleotide-carrier complexes (pCMV/Luc-Pl-ASOR) prepared by the non-disperse method (Panel A) and the improved disperse method (Panel B).

The present invention provides a method for forming polynucleotide-carrier complexes having improved physical characteristics, resulting in greater levels and/or duration of gene expression. The method involves the preparation of essentially unaggregated, homogeneous starting materials which are then combined to form disperse and soluble polynucleotide-carrier complexes.

The present invention also provides a substantially disperse composition of polynucleotide-carrier complexes formed by the above-summarized method. The polynucleotide-carrier complexes are soluble in solution so that, for example, they can easily pass through physiological barriers when administered in vivo to reach target cells or tissues.

The following description will first discuss the components of the polynucleotide-carrier complex, followed by a discussion of the method provided by the present invention for forming the complexes. Also discussed below are various uses for the disclosed polynucleotide-carrier complexes and methods for administering the complexes to cells either in vitro or in vivo.

I Polynucleotides for Use in Polynucleotide-Carrier Complexes

The polynucleotide-carrier complex can contain more than one copy of the same polynucleotide or one or more different polynucleotides. The term "polynucleotide", as used herein, is intended to include any single or double-stranded DNA or RNA molecule, or any analogue thereof. In one embodiment, the polynucleotide is a gene encoding a desired therapeutic protein (e.g., a blood clotting factor, growth factor, enzyme, antagonist, immunogen, cell surface receptor or any other beneficial protein). The gene is generally in a form suitable for expression, processing and secretion by the target cell. For example, to be expressible, the gene must be operably linked to appropriate genetic regulatory elements which are functional in the target cell. Such regulatory sequences include, for example, promoter sequences which drive transcription of the gene. Suitable promoters include a broad variety of viral promoters, such as SV40 and CMV promoters. The gene may also include appropriate signal sequences which provide for trafficking of the encoded protein to intracellular destinations and/or extracellular secretion. The signal sequence may be a natural sequence of the protein or an exogenous sequence.

Regulatory sequences required for gene expression, processing and secretion are artrecognized and are selected to direct expression of the desired protein in an appropriate cell. Accordingly, the term "regulatory sequence", as used herein, includes promoters, enhancers and other expression control elements. Such regulatory sequences are known and discussed in Goeddel, *Gene expression Technology: Methods in Enzymology*, p. 185, Academic Press, San Diego, Calif. (1990). The gene can be contained in an expression vector such as a plasmid or a transposable genetic element along with the genetic regulatory elements necessary for expression of the gene and secretion of the gene-encoded product.

In other embodiments of the invention, the polynucleotide is an antisense polynucleotide (DNA or RNA), or is a gene which is transcribed into an antisense RNA (e.g., a ribozyme). Antisense polynucleotides can be chemically synthesized using standard techniques well known in the art. For example, various methods of chemically synthesizing polydeoxynucleotides are known, including solid-phase synthesis which, like peptide synthesis, has been fully automated in commercially available DNA synthesizers (See e.g., Itakura et al., U.S. Pat. No. 4,598,049; Caruthers et al., U.S. Pat. No. 4,458,066; and Itakura, U.S. Pat. Nos. 4,401,796 and 4,373,071, incorporated by reference herein).

When administered in vivo, synthetic and natural polynucleotides are subject to degradation by exo- and endonucleases in a manner equivalent to any cellular nucleic acid. Accordingly, these polynucleotides can be chemically modified to provide substantial nuclease resistance. Such chemically modified polynucleotides include, for example, phosphorothioate polynucleotides, in which one of the phosphate oxygens is replaced by a sulfur atom (See e.g., U.S. Pat. No: 5,262,530, the teachings of which are incorporated by reference herein). Phosphorothioates may be synthesized using automated techniques employing either phosphoramidite or phosphonate chemistries. Other modified polynucleotides with increased stability include, for example, nonionic DNA analogs, such as alkyl- or arylphosphonates, in which the charged phosphate oxygen is replaced by an alkyl or aryl group (see e.g., U.S. Pat. No: 4,469,863, the teachings of which are incorporated by reference herein), and alkylphosphotriesters, in which the charged oxygen moiety is alkylated (See e.g., U.S. Pat. No: 5,023,243 and European Patent No: 092,574, the teachings of which are incorporated by reference herein). Both of these DNA analogs can be prepared by automated solid-phase synthesis using commercially available reagents. It is also known that addition of a diol, such as tetraethyleneglycol or hexaethyleneglycol, at either or both termini of a synthetic polynucleotide confers substantial nuclease resistance. (See e.g., U.S. Pat. No: 5,245,022, the teachings of which are incorporated by reference herein).

II The Carrier Molecule

The carrier molecule of the polynucleotide-carrier complex performs at least two functions: (1) it binds the polynucleotide in a manner which is sufficiently stable (either in vivo, ex vivo, or in vitro) to prevent significant uncoupling of the polynucleotide extracellularly prior to internalization by a target cell, and (2) it binds to a component on the surface of a target cell so that the polynucleotide-carrier complex is internalized by the cell. Generally, the carrier is made up of a cell-specific ligand and a cationic moiety which, for example are conjugated. The cell-specific ligand binds to a cell surface component, such as a protein, polypeptide, carbohydrate, lipid or combination thereof. It typically binds to a cell surface receptor. The cationic moiety binds, e.g., electrostatically, to the polynucleotide.

The ligand of the carrier molecule can be any natural or synthetic ligand which binds a cell surface receptor. The ligand can be a protein, polypeptide, glycoprotein, glycopeptide or glycolipid which has functional groups that are exposed sufficiently to be recognized by the cell surface component. It can also be a component of a biological organism such as a virus, cells (e.g., mammalian, bacterial, protozoan).

Alternatively, the ligand can comprise an antibody, antibody fragment (e.g., an F(ab')$_2$ fragment) or analogues thereof (e.g., single chain antibodies) which binds the cell surface component (see e.g., Chen et al. (1994) *FEBS Letters* 338:167–169, Ferkol et al. (1993) *J. Clin. Invest.* 92:2394–2400, and Rojanasakul et al. (1994) *Pharmaceutical Res.* 11(12):1731–1736). Such antibodies can be produced by standard procedures.

Ligands useful in forming the carrier will vary according to the particular cell to be targeted. For targeting hepatocytes, proteins and polypeptides containing galactose-terminal carbohydrates, such as carbohydrate trees obtained from natural glycoproteins, can be used. For example, natural glycoproteins that either contain terminal galactose residues or can be enzymatically treated to expose terminal galactose residues (e.g., by chemical or enzymatic desialylation) can be used. In one embodiment, the ligand is an asialoglycoprotein, such as asialoorosomucoid, asialofetuin or desialylated vesicular stomatitis virus.

Alternatively, suitable ligands for targeting hepatocytes can be prepared by chemically coupling galactose-terminal carbohydrates (e.g., galactose, mannose, lactose, arabinogalactan etc.) to nongalactose-bearing proteins or polypeptides (e.g., polycations) by, for example, reductive lactosamination. Methods of forming a broad variety of other synthetic glycoproteins having exposed terminal galactose residues, all of which can be used to target hepatocytes, are described, for example, by Chen et al. (1994) *Human Gene Therapy*

5:429–435 and Ferkol et al. (1993) *FASEB* 7: 1081–1091 (galactosylation of polycationic histones and albumins using EDC); Perales et al. (1994) *PNAS* 91:4086–4090 and Midoux et al. (1993) *Nucleic Acids Research* 21(4):871–878 (lactosylation and galactosylation of polylysine using α-D-galactopyranosyl phenylisothiocyanate and 4-isothiocyanatophenyl β-D-lactoside); Martinez-Fong (1994) *Hepatology* 20(6):1602–1608 (lactosylation of polylysine using sodium cyanoborohydride and preparation of asialofetuin-polylysine conjugates using SPDP); and Plank et al. (1992) *Bioconjugate Chem.* 3:533–539 (reductive coupling of four terminal galactose residues to a synthetic carrier peptide, followed by linking the carrier to polylysine using SPDP).

For targeting the polynucleotide-carrier complex to other cell surface receptors, the carrier component of the complex can comprise other types of ligands. For example, mannose can be used to target macrophages (lymphoma) and Kupffer cells, mannose 6-phosphate glycoproteins can be used to target fibroblasts (fibro- sarcoma), intrinsic factorvitamin B12 and bile acids (See Kramer et al. (1992) *J. Biol. Chem.* 267:18598–18604) can be used to target enterocytes, insulin can be used to target fat cells and muscle cells (see e.g., Rosenkranz et al. (1992) *Experimental Cell Research* 199:323–329 and Huckett et al. (1990) *Chemical Pharmacology* 40(2):253–263), transferrin can be used to target smooth muscle cells (see e.g., Wagner et al. (1990) *PNAS* 87:3410–3414 and U.S. Pat. No. 5, 354,844 (Beug et al.)), Apolipoprotein E can be used to target nerve cells, and pulmonary surfactants, such as Protein A, can be used to target epithelial cells (see e.g., Ross et al. (1995) *Human Gene Therapy* 6:31–40).

The cationic moiety of the carrier molecule can be any positively charged species capable of electrostatically binding to negatively charged polynucleotides. Preferred cationic moieties for use in the carrier are polycations, such as polylysine (e.g., poly-L-lysine), polyarginine, polyornithine, spermine, basic proteins such as histones (Chen et al., supra.), avidin, protamines (see e.g., Wagner et al., supra.), modified albumin (i.e., N-acylurea albumin) (see e.g., Huckett et al., supra.) and polyamidoamine cascade polymers (see e.g., Haensler et al. (1993) *Bioconjugale Chem.* 4: 372–379). A preferred polycation is polylysine (e.g., ranging from 3,800 to 60,000 daltons).

In one embodiment, the carrier comprises polylysine having a molecular weight of about 17,000 daltons (purchased as the hydrogen bromide salt having a MW of a 26,000 daltons), corresponding to a chain length of approximately 100–120 lysine residues. In another embodiment, the carrier comprises a polycation having a molecular weight of about 2,600 daltons (purchased as the hydrogen bromide salt having a MW of a 4,000 daltons), corresponding to a chain length of approximately 15–10 lysine residues.

III Forming the Carrier Molecule

The carrier can be formed by linking a cationic moiety and a cell-specific ligand using standard cross-linking reagents which are well known in the art. The linkage is typically covalent. A preferred linkage is a peptide bond. This can be formed with a water soluble carbodiimide, such as 1-ethyl-3-(3-dimethylaminopropyl)carbodiimide hydrochloride (EDC), as described by McKee et al (1994) *Bioconjugate Chem.* 5: 306–311 or Jung, G. et al. (1981) *Biochem. Biophys. Res. Commun.* 101: 599–606 or Grabarek et al. (1990) *Anal. Biochem.* 185:131. Alternative linkages are disulfide bonds which can be formed using cross-linking reagents, such as N-Succinimidyl 3-(2-pyridyldithio) propionate (SPDP), N-hydroxysuccinimidyl ester of chlorambucil, N-Succinimidyl-(4-Iodoacetyl) aminobenzoate) (SIAB), Sulfo-SIAB, and Sulfo-succinimidyl-4-maleimidophenyl-butyrate (Sulfo-SMPB). Strong noncovalent linkages, such as avidin-biotin interactions, can also be used to link cationic moieties to a variety of cell binding agents to form suitable carrier molecules.

The linkage reaction can be optimized for the particular cationic moiety and cell binding agent used to form the carrier. The optimal ratio (w:w) of cationic moiety to cell binding agent can be determined empirically. This ratio will vary with the size of the cationic moiety (e.g., polycation) being used in the carrier, and with the size of the polynucleotide to be complexed. However, this ratio generally ranges from about 0.2–5.0 (cationic moiety ligand). Uncoupled components and aggregates can be separated from the carrier by molecular sieve or ion exchange chromatography (e.g., Aquapore™ cation exchange, Rainin).

In one embodiment of the invention, a carrier made up of a conjugate of asialoorosomucoid and polylysine is formed with the cross linking agent 1-(3-dimethylaminopropyl)-3-ethyl carbodiimide. After dialysis, the conjugate is separated from unconjugated components by preparative acid-urea polyacrylamide gel electrophoresis (pH 4-5). The conjugate can be further purified on the carboxymethyl functionalized column (see U.S. patent application Ser. No.08/043,008, filed Apr. 5, 1993, now abandoned, the teachings of which are incorporated by reference herein).

IV. Formation of Polynucleotide-Carrier Complexes

According to the method of the present invention, polynucleotide-carrier complexes are formed using unaggregated starting materials which, when combined, form soluble complexes which are substantially disperse and homogenous in size. These characteristics contribute to high levels and duration of expression, likely due to the fact that smaller, less aggregated complexes are more easily internalized into endosomes of target cells and are also less likely to be taken up by macrophages. In addition, substantially disperse polynucleotide-carrier complexes will more easily pass through physiological barriers, such as blood/tissue barriers and small capillary systems.

The term "substantially disperse" or "substantially unaggregated," as used herein, refers to polynucleotide-carrier complexes having one or more of the following characteristics:

(1) the complexes have an average radius, as measured by laser light scattering, of about 120 nm or less, preferably about 100 nm or less, more preferably about 90–40 nm or less, and most preferably about 60–30 nm or less;

(2) the carrier component of the complexes have an average radius, as measured by laser light scattering, of about 20 nm or less, preferably about 15 nm or less and most preferably about 10 nm or less;

(3) the complexes exhibit little to no aggregation and a substantial degree of homogeneity on agarose gels of sucrose density gradient fractions prepared as described herein (e.g., do not appear to any substantial degree at the bottom of the sucrose gradient and are concentrated toward the top 50–25% of the gradient);

(4) the complexes exhibit improved levels and/or duration of expression, as compared to complexes formed by the non-disperse method described in the following Examples;

(5) the complexes exhibit little turbidity in solution; and (6) the complexes exhibit an increase (e.g., of about 5–90%) in the percent of complex recovered following 0.2μ filtration, as compared to complexes formed by the non-disperse method described in the following Examples.

In forming the polynucleotide-carrier complex, the carrier molecule is linked to the polynucleotide so that (a) the polynucleotide is sufficiently stable (either in vivo, ex vivo, or in vitro) to prevent significant uncoupling of the polynucleotide extracellularly prior to internalization by the target cell, (b) the polynucleotide is released in functional form under appropriate conditions within the cell, (c) the polynucleotide is not damaged and (d) the carrier retains its capacity to bind to cells. Generally, the linkage between the carrier and the polynucleotide is noncovalent. Appropriate noncovalent bonds include, for example, electrostatic bonds, hydrogen bonds, hydrophobic bonds, anti-polynucleotide antibody binding, linkages mediated by intercalating agents, and streptavidin or avidin binding to polynucleotide-containing biotinylated nucleotides. However, the carrier can also be directly (e.g., covalently) linked to the polynucleotide using, for example, chemical cross-linking agents (e.g., as described in WO-A-91/04753 (Cetus Corp.), entitled "Conjugates of Antisense Oligonucleotides and Therapeutic Uses Thereof").

To form polynucleotide-carrier complexes, a solution containing essentially unaggregated carrier molecules is combined with a polynucleotide to be complexed. The solution contains a sufficient amount of a charge shielding agent to inhibit aggregation of the carrier molecules (i.e., aggregation which would occur in the absence of a charge shielding agent). In one embodiment, the carrier solution is prepared by forming carrier molecules, as described above (e.g., by conjugation of a cationic moiety and a cell binding agent), and then mixing the carrier molecules with a sufficient amount of a charge shielding agent to inhibit aggregation of the carrier molecules.

The term "charge shielding agent", as used herein, is intended to include any agent which is capable of (a) reducing charge interactions (e.g., hydrogen bonding) between individual cationic carrier molecules and/or between different parts of the same carrier molecule; and/or (b) reducing charge interactions between cationic carrier molecules and the solvent.

The term "inhibit aggregation," as used herein, refers to disaggregation and/or to prevention of aggregation of cationic carrier molecules.

The terms "essentially unaggregated carrier molecules" and "sufficient to inhibit aggregation of the carrier molecules," as used herein, refer to a level of disaggregation at which the carrier molecules, when complexed to polynucleotide, are easily taken up by cells and/or can easily pass through physiological barriers (e.g., blood/tissue barriers). Generally, this level of dispersity is achieved when the carrier molecules have a radius of about 20 nm or less, preferably about 15 nm or less and most preferably about 10 nm or less, as measured by laser light scattering analysis. Other methods of determining the level of aggregation of carrier molecules (alone or complexed to polynucleotide) include, for example, sucrose density gradient analysis, electron microscopy (EM), circular dichroism (CD), and spectrophotometry (e.g., absorbance at 260 nm).

In a preferred embodiment of the invention, the charge shielding agent is a salt. Suitable salts include, for example, sodium chloride (NaCl), sodium sulfate ($Na_2SO_4$), sodium phosphate ($NaH_2PO_4$), ammonium sulfate (($NH_4$)$SO_4$), ammonium phosphate ($NH_4H_2PO_4$), potassium sulfate ($K_2SO_4$), potassium phosphate ($KH_2PO_4$), potassium chloride (KCl), magnesium sulfate ($MgSO_4$), magnesium phosphate ($MgHPO_4$), magnesium chloride ($MgCl_2$), and lithium chloride (LiCl) and a variety of others. In a particularly preferred embodiment, the salt is sodium chloride (NaCl).

Other charge shielding agents which can be used to substantially disaggregate the carrier molecules include, for example, detergents and amphiphile surfactants such as the BRIJ family of polyoxyethylene fatty ethers, the SPAN sorbitan fatty acid esters, and the TWEEN polyoxyethylene derivatives of sorbitan fatty acid esters, all available from ICI Americas, Inc. of Wilmington, Del.

When using a salt (e.g., NaCl) as the charge shielding agent, the appropriate amount of salt to inhibit aggregation of the carrier molecules will vary according to the concentration of the carrier molecules. However, this concentration is generally at least about 1.0 M or more. For example, for solutions containing carrier molecules at a concentration of about 0.5–20 mg/mL, the salt can be added to a concentration of about 1.0–10 M. In a preferred embodiment, the carrier molecules are present in the carrier solution at a concentration of about 3.0–7.0 mg/mL, preferably about 5.0–6.0 mg/mL, and most preferably about 5.6 mg/mL. At these concentrations of carrier molecules, the carrier solutions can be prepared with salt concentrations of about 1.0–5.0 M, preferably about 4.0–5.0 M, and most preferably about 4.7 M, respectively.

However, the appropriate amount of any given charge shielding agent to inhibit aggregation of carrier molecules can be determined empirically. For example, samples of carrier molecules can be prepared at various concentrations of a charge shielding agent as previously described, and the level of aggregation of the carrier molecules can then be examined by any of the techniques disclosed above (e.g., laser light scattering analysis, sucrose density gradient analysis, electron microscopy (EM), circular dichroism (CD), and spectrophotometry)

In addition to a charge shielding agent, the carrier solution can also optionally contain other dispersing agents to further inhibit aggregation of the carrier molecules. As previously discussed, aggregation of cationic carrier molecules is believed to result largely from intermolecular and intramolecular associations (e.g., hydrogen bonding) involving the net positive charge of the carrier molecules. Agents which reduce the net positive charge of the carrier molecules, therefore, can diminish these molecular associations and promote dispersity of the cationic carrier molecules.

Accordingly, in one embodiment of the invention, the carrier solution comprises a charge neutralizing agent, in addition to the charge shielding agent. The term "charge neutralizing agent", as used herein, is intended to include any agent capable of neutralizing a portion of the positive charge of cationic carrier molecules (i.e., by deprotonation). In a preferred embodiment of the invention, the charge neutralizing agent is a base. Suitable bases include, for example, sodium hydroxide (NaOH), potassium hydroxide (KOH), ammonium hydroxide ($NH_4OH$), alkylamines, alkoxides and triethanolamines. In a particularly preferred embodiment, the base is sodium hydroxide.

The cationic carrier solution contains the charge neutralizing agent in an amount sufficient to neutralize a portion of the positive charge of the carrier molecules. This partial neutralization reduces charge associations and aggregation of the carrrier molecules, while still maintaining an overall net positive charge associated with the carrier molecules (so that they are able to electrostatically bind negatively charged polynucleotides). In one embodiment of the invention, the charge neutralizing agent is added to the carrier solution in an amount sufficient to neutralize about 5 to 20% (e.g., about 10%) of the positive charge of the carrier molecules. The charge neutralizing agent may be added to the carrier solution before, after or concurrently with the charge shielding agent.

When using a base as the charge neutralizing agent, the carrier solution can be prepared with a concentration of base (e.g., NaOH) of about 10–1000 mM, preferably about 10–100 mM, more preferably about 50–70 mM, and most preferably about 59 mM, for carrier solutions containing carrier molecules at a concentration of about 0.5–20 mg/mL, preferably about 3–7 mg/mL, more preferably about 5–6 mg/mL, and most preferably about 5.6 mg/mL, respectively. The carrier solution can then be mixed vigorously to promote disaggregation of molecular carrier aggregates.

The polynucleotide to be complexed is combined (and allowed to equilibrate) with the carrier solution to form substantially disperse and soluble polynucleotide-carrier complexes. The polynucleotide is combined with the carrier solution so that the polynucleotide-carrier solution contains a final concentration of charge shielding agent and, optionally, charge neutralizing agent which does not damage or induce any substantial conformational change (e.g., denature) in the polynucleotide so that it remains substantially functional and in a form suitable for complexing with the carrier molecules. Generally, this corresponds to a final concentration of charge shielding agent (e.g., salt) of less than 1.0 M, preferably less than 0.75 M, and most preferably less than 0.5 M (e.g., about 0. 15–0.5 M), and a concentration of charge neutralizing agent of less than 10 mM, preferably less than 4.0 mM, and most preferably about 2.0 mM.

In one embodiment, the polynucleotide is diluted, for example, with nanopure water, prior to (or concurrently with) being combined with a carrier solution to a concentration which, when combined with the carrier solution, results in the desired final concentration of charge shielding agent (e.g., salt) and charge neutralizing agent (e.g., base). When adding the polynucleotide to a carrier solution containing a salt (e.g., NaCl) as the charge shielding agent, the polynucleotide can be diluted to a concentration which results in a final salt concentration (i.e., after mixing with carrier solution) of less than 1.0 M, preferably less than 0.5 M, more preferably about 0.15–0.5 M and most preferably about 0.3 M (about two times physiological). At this concentration of salt, the carrier molecules maintain a high level of dispersity and the polynucleotide remains functional.

If the carrier solution contains a charge neutralizing agent (e.g., a base), along with the charge shielding agent, then the final concentration of charge neutralizing agent in the carrier solution, following addition of the polynucleotide, should also be a concentration which does not substantially damage, alter, or inhibit the function of the polynucleotide. For example, when using a base as the charge neutralizing agent, the polynucleotide-carrier solution can contain a final base concentration of less than 50 mM, preferably less than 10 mM, more preferably less than 4.0 mM (e.g., about 1.0–4.0 mM), and most preferably about 2.0 mM.

In a preferred embodiment of the invention, the final solution in which the polynucleotide-carrier complexes are formed has (a) a carrier molecule concentration of about 3.0–7.0 mg/mL, preferably about 5.0–6.0 mg/mL, (b) a salt concentration of about 0.15–0.5 M, preferably about 0.3 M, (c) a base concentration of about 1.0–4.0 mM, preferably about 2.0 mM and (c) an appropriate final concentration of DNA (e.g., 10 µg/mL).

The polynucleotide is combined with the carrier solution in an amount appropriate to form stable complexes which remain soluble in solution. Generally, the polynucleotide is added to the carrier solution in a weight to weight (w:w) ratio (polynucleotide to carrier) of about 1:0.2–1:20, (e.g., about 1:1–1:10, or about 1:1.5–1:5). Complexes formed with these weight ratios (polynucleotide to carrier) have corresponding charge neutralization ratios (i.e., percent neutralization of negatively charge polynucleotide by positively charged carrier) of about 10–1000% (e.g., about 50–500%, or about 75–250%), respectively.

As described in Example 4 below, the performance of a given polynucleotide-carrier complex can be affected by the level of polynucleotide charge neutralization in the complex. The optimal level of polynucleotide charge neutralization for a given complex can depend on a variety of factors, including the nature of the polynucleotide (e.g., DNA vs. RNA), the size of the polynucleotide (e.g., plasmid DNA vs. antisense oligonucleotide) and the size and charge of the particular cationic carrier molecule used. While appropriate levels of polynucleotide charge neutralization for complexes generally fall within the ranges provided above, the optimal level for a given complex can be determined empirically. For example, as demonstrated in Example 4, a series of preparations can be made for a particular complex (e.g., pCMV/Luc-Pl-ASOR), each with varying degrees of polynucleotide charge neutralization. The performance of these samples can then be tested by, for example, measuring levels of expression obtained with each sample either in vitro or in in vivo expression assays.

Figure 7:
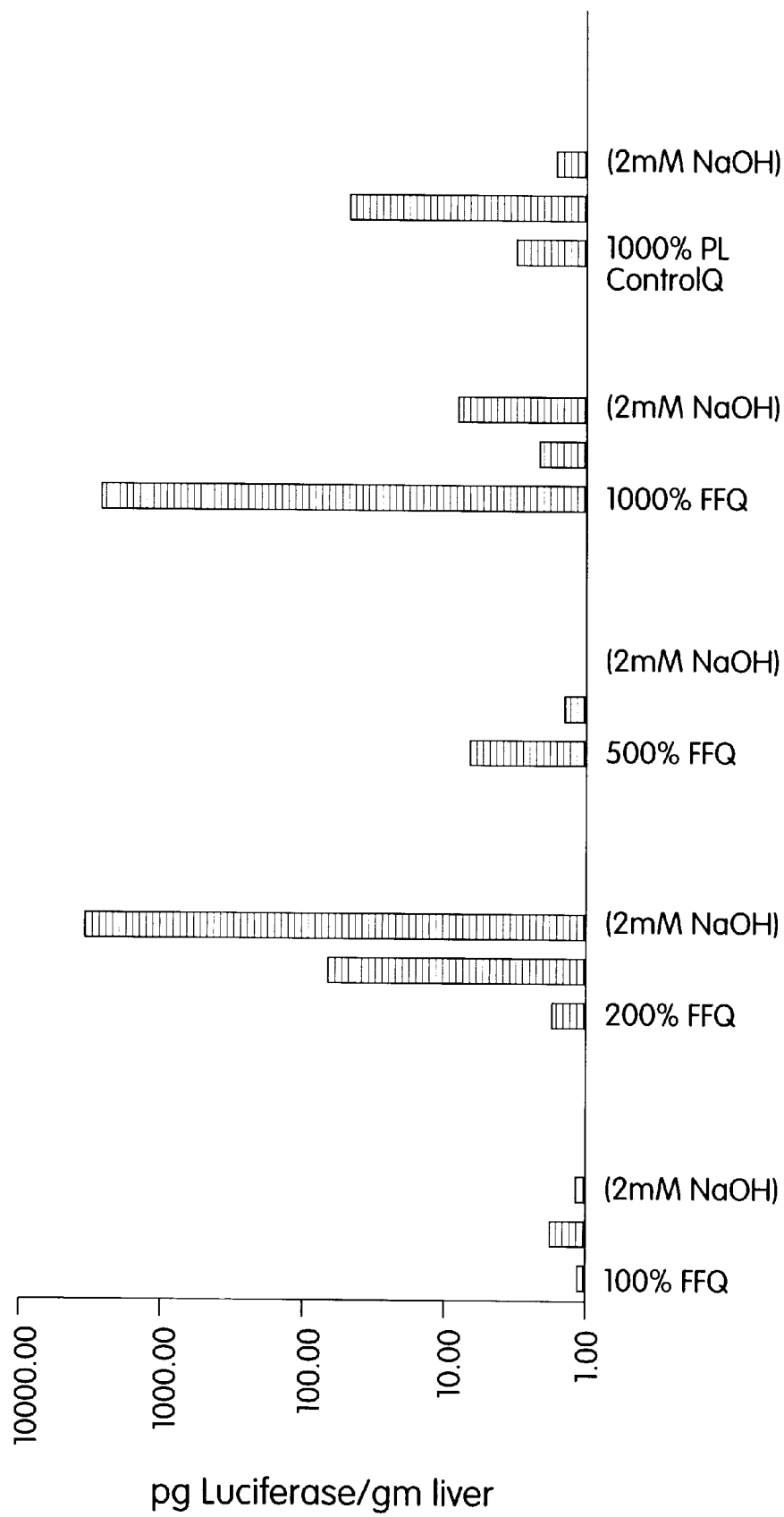
FIG. 7 is a graphic representation of luciferase expression levels obtained from complexes of pCMV/Luc-Pl-ASOR formed by the improved disperse method. Complexes were prepared with varying percentages (100%, 200%, 500% or 1000%) of charge neutralization of negatively charged DNA by positively charged polycation. A complex of pCMV/Luc and free polylysine (pCMV/Luc-Pl) having a 1000% charge neutralization ratio was used as a control. Mice were injected in triplicate with complex. After 5 days, mice were sacrificed and their livers were assayed for luciferase activity.

When forming complexes containing plasmid DNA linked to polylysine-ASOR carrier molecules, more anionic (e.g., 50% neutralized) or more cationic (e.g., 200%, 500% and 1000% neutralized) complexes have been found in the Examples described below to achieve higher levels of expression than more neutral (e.g., 100%) complexes which have a proportionately larger hydrophobic component (see e.g., FIG. 7). In addition, as shown in FIG. 7, the presence of ASOR in the complex can also significantly increase expression, probably due to its increasing the solubility of the complex (it is likely that the hydrophobic nature of the unconjugated polylysine is detrimental to the overall performance of the complex). For example, as shown in FIG. 7, a 1000% neutralized DNA-Pl complex exhibits far lower expression than does a 1000% neutralized DNA-Pl-ASOR complex.

Compositions containing substantially disperse and soluble polynucleotide-carrier complexes which exhibit significant levels and duration of expression can be prepared using the method described in detail above. However, additional steps also can be taken which further diminish aggregation of complexes, as well as reduce the size of the complexes and increase their homogeneity, thereby improving their performance (e.g., level of gene expression). Such measures include, for example, extrusion of the complexes, temperature variations, pH changes and measures which diminish inhibitory actions which occur in vivo (e.g., opsonization of the complex by inhibitory factors present in blood serum).

Accordingly, in another embodiment of the invention, the complexes are extruded through an appropriate filter after being formed but prior to being administered to cells (either in vitro or in vivo). The term "extrusion" or "extruded", as used herein, means passage of the complexes through a filtering apparatus, followed by collection of the filtered product.

Figure 10A:
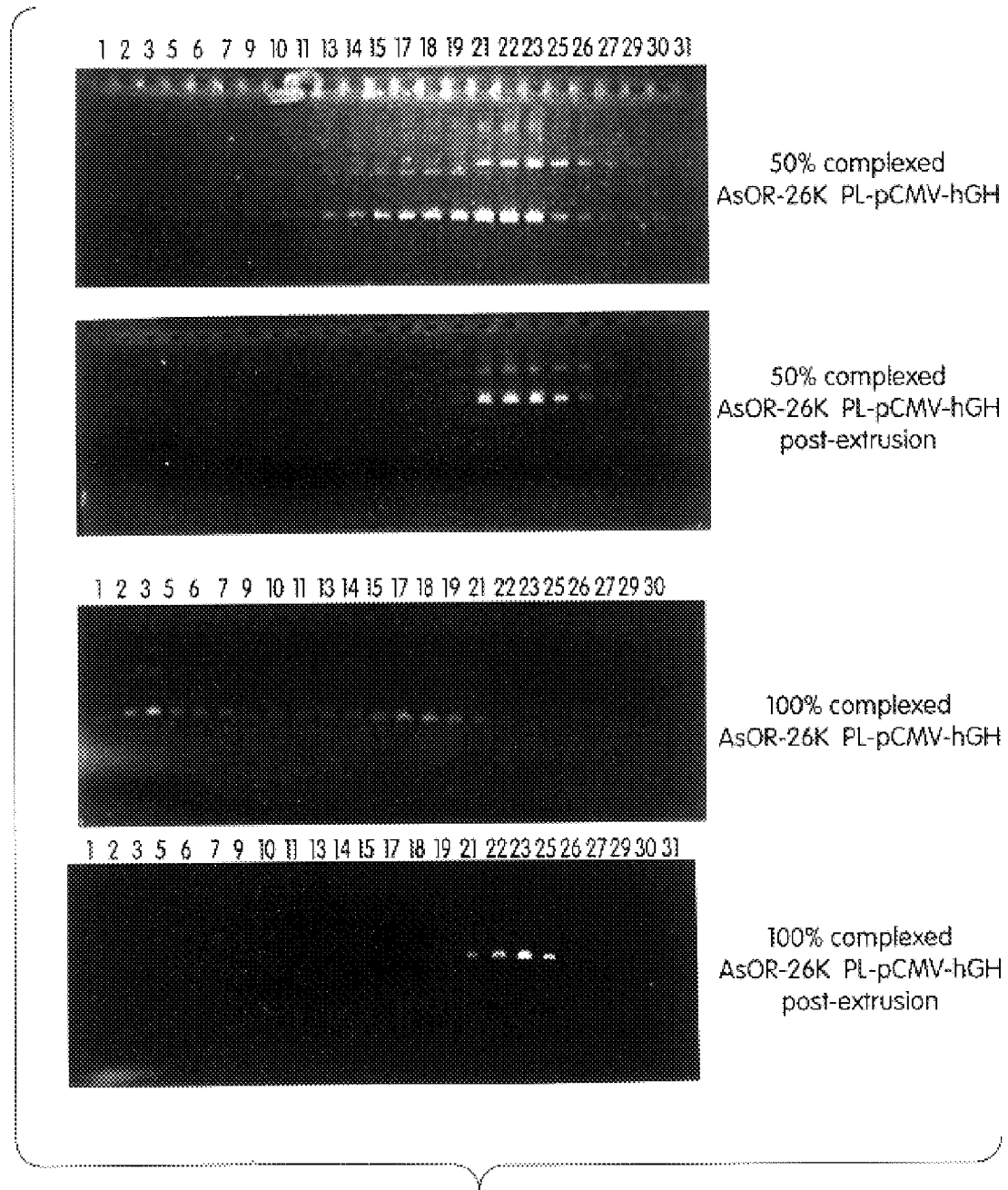
FIGS. 10(a) and 10(b) show a comparison of agarose gels of sucrose density gradient fractions containing extruded and non-extruded pCMV/hGH-Pl-ASOR complexes having varying degrees of charge neutralization (50%, 100%, 250% and 500%).
Figure 10B:
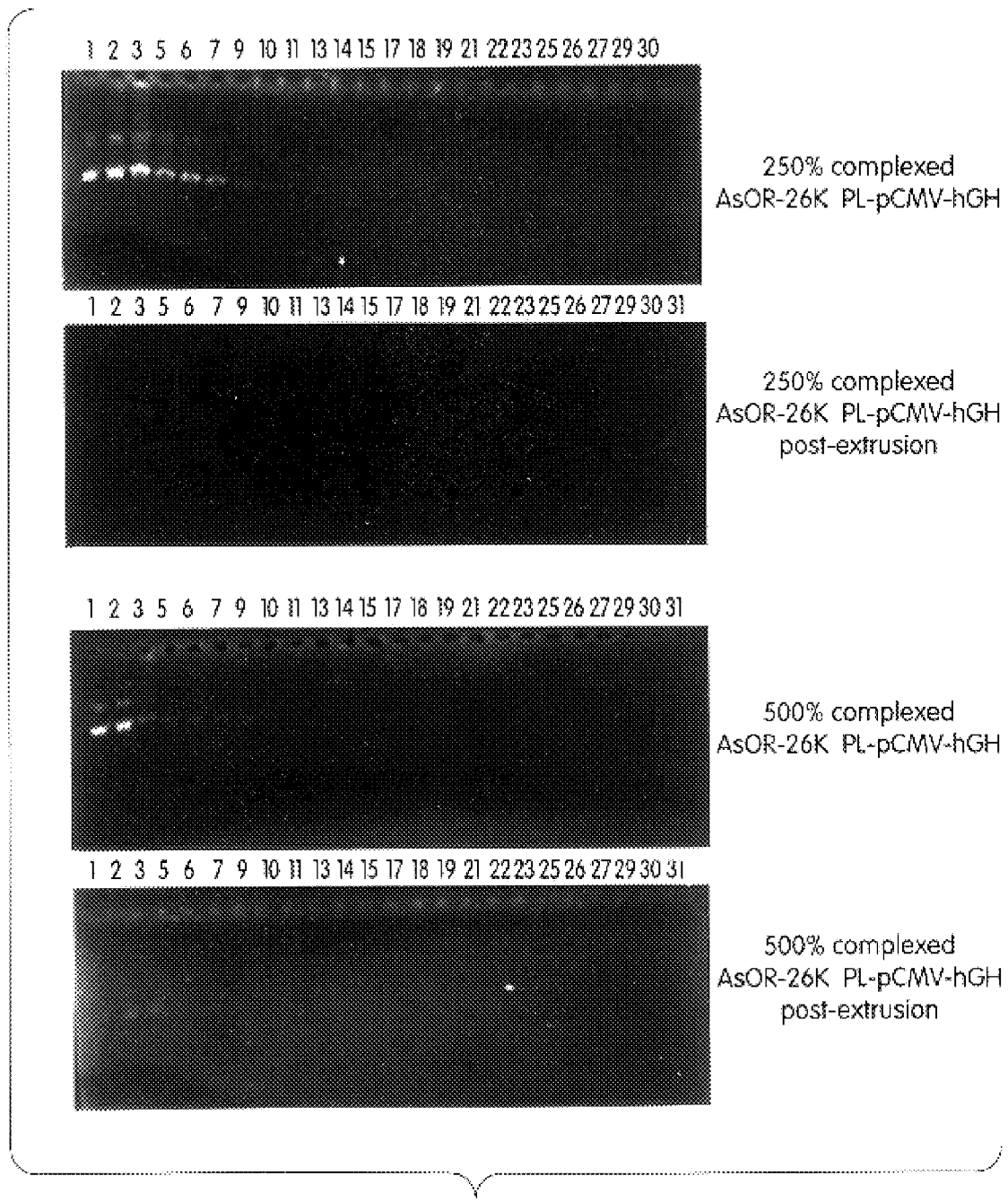

As demonstrated in Example 5, extrusion of complexes significantly (1) decreases the size of the complexes (see Table 3 and FIGS. 10(a) and 10(b)), (2) increases the homogeneity of the complexes (see Table 3 and FIGS. 10(a) and 10(b)), and (3) improves the performance of the complexes (see Table 4 and FIG. 8), as measured by gene expression levels. While any extrusion apparatus which diminishes larger complexes and increases the proportion of smaller, more homogenous complexes may be used, a preferred apparatus for extruding complexes is a 50 nm filter attached to an Emulsi-Flex-C5 (Avestin, Inc. Ottowa, Canada).

V Uses And Administration of Polynucleotide-Carrier Complexes

Compositions of substantially disperse and homogenous polynucleotide-carrier complexes formed by the methods the present invention can be used in a variety of diagnostic and therapeutic methods involving transfer of polynucleotides to cells. For example, the complexes can be used to selectively deliver polynucleotides (e.g., genes, antisense constructs and diagnostic polynucleotides) to target cells under a variety of conditions. In some cases, it may be advantageous to administer the polynucleotide as a free (i.e., not complexed) nucleic acid as described in the examples below.

For in vitro delivery of a polynucleotide, cultured cells can be incubated with the polynucleotide-carrier complexes of the invention in an appropriate medium under conditions conducive to endocytotic uptake by the cells.

Polynucleotides can also be delivered ex vivo to cells or tissues which have been removed from an organism, incubated with polynucleotide-carrier complexes of the invention, and then returned to the organism.

For in vivo delivery of a polynucleotide to a cell, the polynucleotide-carrier complexes of the invention can be administered to a subject in a pharmaceutically acceptable vehicle. The term "pharmaceutically acceptable carrier", as used herein, is intended to include any physiologically acceptable carrier for stabilizing polynucleotide-carrier complexes of the present invention for administration in vivo, including, for example, saline and aqueous buffer solutions, solvents, dispersion media, antibacterial and anti-fungal agents, isotonic and absorption delaying agents, and the like. The use of such media and agents for harmaceutically active substances is well known in the art. Except insofar as any conventional media is incompatible with the polynucleotide-carrier complexes of the present invention, use thereof in a therapeutic composition is contemplated.

In all cases, the pharmaceutical composition must be sterile and must be fluid to the extent that easy syringability exists. It must be stable under the conditions of manufacture and storage and must be preserved against the contaminating action or microorganisms such as bacteria and fungi. Protection of the polynucleotide-carrier complexes from degradative enzymes (e.g., nucleases) can be achieved by including in the composition a protective coating or nuclease inhibitor. Prevention of the action of microorganisms can be achieved by various anti-bacterial and anti-fungal agents, for example, parabens, chlorobutanol, phenol, ascorbic acid, thimerosal, and the like.

The poly- or oligonucleotides of the invention can also be protected from degradative enzymes by encapsulation into liposomes. These delivery vehicles are comprised of one or more spherical lipid bilayers, typically phospholipid bilayers, which protect the drugs they encapsulate. Once administered to a subject, the liposomes are taken up by cells via endocytosis and the drugs they contain are released therein. (See e.g., WO 92/06192, the teachings of which are incorporated by reference herein).

Polynucleotide-carrier complexes of the invention may be administered in vivo by any suitable route of administration. The appropriate dosage may vary according to the selected route of administration. The complexes are preferably injected intravenously in solution containing a pharmaceutically acceptable carrier, as defined herein. Sterile injectable solutions can be prepared by incorporating the polynucleotide-carrier complexes in the required amount in an appropriate buffer with one or a combination of ingredients enumerated above, as required, followed by filtered sterilization. Other suitable routes of administration include intravascular, subcutaneous (including slow-release implants), topical and oral.

Appropriate dosages may be determined empirically, as is routinely practiced in the art. Mice can be administered dosages of up to 1.0 mg of polynucleotide per 20 g of mouse, or about 1.0 mL of complex per 1.4 mL of mouse blood.

This invention is illustrated further by the following examples which should not be construed as further limiting the subject invention. The contents of all references and published patent applications cited throughout this application are hereby incorporated by reference.

EXAMPLES

MATERIALS AND METHODS

Protamine, Poly-L-lysine (26kD; mean MW) and Bovine Serum Albumin (BSA) were purchased from Sigma Chemical Co., St. Louis, Mo. 1-[3-(dimethylamino)-propyl]-3-ethylcarbodiimide (EDC) was purchased from Aldrich Chemical Co, Milwaukee, Wis. Orosomucoid was purchased from Alpha Therapeutics, Los Angeles, Calif. Asialoorosomucoid (ASOR) was prepared from orosomucoid (15 mg/ml) by hydrolysis with 0.1N sulfuric acid at 76° C. for one hour. ASOR was purified from the reaction mixture by neutralization with 1.0 N NaOH to pH 5.5 and exhaustive dialysis against water at room temperature. ASOR concentration was determined using an extinction coefficient of 0.92 mL mg$^{-1}$, cm$^{-1}$ at 280 nm. The thiobarbituric acid assay of Warren (1959) *J. Biol. Chem.* 234: 1971–1975 was used to verify desialylation of the OR. ASOR prepared by the above method was determined to be 98% desialylated.

ASOR-poly-L-lysine conjugate (AP26K) was prepared by carbodiimide coupling similar to that reported by McKee et al (1994) *Bioconjugate Chem.* 5: 306–311. ASOR, 26 kD poly-L-lysine and EDC in a 1:1:0.5 mass ratio were reacted as follows. EDC (dry) was added directly to a stirring aqueous ASOR solution. 26 kD Polylysine was added and the reaction mixture was adjusted to pH 5.5–6.0 and stirred for two hours at ambient temperature. ASOR concentration was 5 mg/mL in the final reaction conditions. The reaction was quenched by addition of Na$_3$PO$_4$ (200 mM, pH 11) to a final concentration of 10 mM. The conjugate was first purified on a Fast Flow Q Sepharose anion exchange chromatography column (Pharmacia) eluted with 50 mM Tris, pH 7.5, and then dialyzed against water. BSA-poly-L-lysine was prepared by the same process.

Human growth hormone kit and antibodies were obtained from Nichols Institute Diagnostics, San Juan Capistrano, Calif.

Standards and reagents for luciferase assays were purchased from Analytical Luminescence Laboratories, San Diego, Calif.

Plasmids pCMV-Luciferase has been described previously by Merwin et al. (1994) *Bioconj. Chem.* 5: 612–620. pCMV-hGH was constructed by taking the Bam H1-Spe 1 fragment of pcDNA1 Amp plasmid (InVitrogen) containing the CMV promoter and ligating it to p0hGH (Nichol's Institutional Diagnostics) which had been digested with Bam H1 and Xba 1.

Plasmid DNA was prepared by the alkaline lysis method using Giga DNA kits from Qiagen Chatsworth, Calif. Endotoxin was removed from plasmid DNA preparations using the endotoxin kit from Qiagen.

Polynucleotide-Carrier Complex Formation Using the Disperse Method

All polynucleotide-carrier complexes and controls were prepared under identical conditions. In each case the carrier, at a concentration of about 3.0–7.0 mg/mL (e.g., about 5.0–6.0), was aliquoted into a reaction vessel to which was added an amount of 5 M NaCl to obtain a final concentration of between 4.0–5.0 M NaCl and an amount of 1 M NaOH to obtain a final concentration of between 50–100 mM NaOH.

The carrier was most commonly at a concentration of about 5.6 mg/ml. In this case, the carrier was combined with an amount of 5 M NaCl to obtain a final concentration of about 4.7 M NaCl and an amount of 1 M NaOH to obtain a final concentration of about 59 mM NaOH. The solutions were mixed vigorously.

The desired plasmid in 10 mM Tris-HCl, 1 mM EDTA buffer was diluted by adding nanopure water and then combined with the carrier solution to achieve a final concentration of 300 mM NaCl and 2 mM NaOH.

In the case of free DNA, no polycation was used and all other steps were identical.

Polynucleotide-Carrier Complex Formation Using the Non-Disperse Method

All non-disperse polynucleotide-carrier complexes and controls were prepared under identical conditions. In each case the desired plasmid in 10 mM Tris-HCl, 1 mM EDTA buffer was aliquoted into a reaction vessel containing the required amounts of 5 M NaCl and nanopure water to obtain a DNA concentration of 10 $\mu$g/mL and a final salt concentration (i.e., following addition of the DNA) of about 0.15 M. The solution was mixed vigorously. The carrier in nanopure water was then rapidly added to the DNA solution.

All non-disperse polynucleotide-carrier complexes were formed in 0.15 M NaCl at a final DNA concentration of 10 $\mu$g/mL.

In the case of free DNA, no polycation was used and all other steps were identical.

Extrusion of Polynucleotide-carrier complexes

Complexes were extruded through a 50 nm filter attached to an Emulsi-Flex-C5 (Avestin, Inc. Ottowa, Canada).

Neutralization Ratios

Purified conjugates were exhaustively dialyzed against ultra-pure water. An aliquot of the dialyzed conjugate solution was lyophilized, weighed and dissolved in ultra-pure water at a specific concentration (w/v). Since polylysine has minimal absorbance at 280 nm, the ASOR component of the conjugate (w/v) was calculated using the extinction co-efficient at 280 nm. The composition of the conjugate was estimated by comparison of the concentration of the conjugate (w/v) with the concentration of ASOR (w/v) as determined by UV absorbance. The difference between the two determinations was attributed to the polylysine component of the conjugate. The ratio of conjugate to DNA (w:w) necessary for charge neutralization was then calculated using the determined cationic composition.

Neutralization ratios for protamine conjugates were calculated from the known molecular structure of protamine.

Biodistribution Assay

ASOR-poly-L-lysine conjugate (AP26K) was radiolabeled with $^{125}$Iodine by the Iodogen method (Pierce, Rockford, Ill.). The radiolabeled AP26K was purified over a G-25 desalting column (Pierce) to give a specific activity of 8 $\mu$Ci/$\mu$g. The radiolabeled AP26K was mixed with pCMV-Luciferase following the method above to form a DNA-carrier complex, hereafter referred to as the GeneDrug™ complex.

Approximately 1 $\mu$g of the GeneDrug™ complex was injected via tail vein into mice. The mice were sacrificed by cervical dislocation 5 minutes post-injection and the organs were harvested. The intact organs were counted in a gamma counter and a percent of the total dose per organ was calculated by comparison to a standard generated from the preinjection material. All assays were done in triplicate.

For competition studies the competing ligand (ASOR or dextran sulfate) was coinjected with the radiolabeled GeneDrug™ complex.

Animals

Mice were injected in the tail vein with plasmid DNA in the form of free DNA or a DNA-carrier complex. The dose was 10 $\mu$g of DNA per mouse except as noted for the extruded complex studies described below. To assay for Luciferase or $\beta$-Galactosidase expression, mice were sacrificed at a specified timepoint by cervical dislocation and the appropriate organs were removed. To assay for levels of human growth hormone (hGH), 200 $\mu$l of mouse blood was collected by retro-orbital capillary puncture.

Luciferase Expression Assay

For each organ assayed (i.e., liver, spleen, kidney, heart and lung), the entire organ was excised and placed into 50 mL centrifuge tube containing phosphate-buffered saline (PBS). The organ was rinsed twice with PBS. Organ weight was determined gravimetrically and recorded. Ten volumes of cell lysis buffer (100 mM potassium phosphate pH 7.8, 0.2% Triton X-100) were added to the organ and it was homogenized by douncing. 1 mL of cell lysate was spun for 5 minutes at maximum speed in a microcentrifuge tube. The clear liquid interface was collected from between the fat layer on top and the cell pellet on the bottom of the tube. This clear liquid was centrifuged for an additional 5 minutes at high speed. The luciferase assay was performed on 5–10 mL of the final supernatant.

Luciferase activity of aliquots of tissue homogenate was measured using an Analytical Luminescence 2010 Luminometer (Hickman et al. (1994) *Human Gene Therapy* 5: 1477–1483. Activity was background subtracted and converted to picograms of protein. The conversion was calculated from standard curves based on purified luciferase protein standards (Analytical Luminescence Laboratories).

$\beta$-Galactosidase Expression Assay

The entire mouse liver was perfused with PBS to remove any red blood cells. The liver became white. The organ was rinsed twice with PBS. Organ weight was determined gravimetrically and recorded. One volume of cell lysis buffer (100 mM potassium phosphate pH 7.8, 0.2% Triton X-100) were added to the organ and it was homogenized by douncing. A liver from a control animal was harvested and treated in the same manner. 1 mL of cell lysate was spun for 5 minutes at level 14 in a microcentrifuge tube. The clear liquid was collected from the interface between the fat layer on top and the cell pellet on the bottom of the tube. The clear liquid was spun for an additional 5 minutes at high speed.

$\beta$-galactosidase expression was measured as described by Guzman et al. (1993) *Circ. Res.* 73: 1202–1207. Specifically, 30 $\mu$L of the cell lysate was added (to a total volume of 300 $\mu$L) to 1.0 mM MgCl$_2$, 45 mM $\beta$-mercaptoethanol, 67 mM sodium phosphate, pH 7.5, 3.52 mg/ml chlorophenolred $\beta$-D-galactopyranoside (CRPG, Boehringer Mannheim, Indianapolis, Ind.). The reaction was incubated for one hour at 37° C. and then 500 $\mu$L of 1.0 M sodium carbonate was added to stop the reaction. The absorbance of the reaction was read at 570 nm. Purified β-galactosidase (Sigma Chemicals) was used to prepare a standard curve.

Human Growth Hormone (hGH) Expression Assay

Serum samples collected from mice as described above were prepared by clotting and spinning. The serum was assayed for levels of hGH by ELISA following the method of Zatloukal et al. (1994) PNAS 91: 5148–5152. Murine growth hormone interference was shown to be nugatory and serum from untreated mice was used as a negative control.

Sucrose Gradient and Agarose Gel Analyses

Sucrose gradients were prepared as 5–30% gradients in SW40 polyallomer tubes with a 0.5 ml CsCl cushion (p>1.88). The sucrose loading mixtures were dissolved in a NaCl concentration appropriate for the samples being analyzed. One mL samples containing 10 μg DNA or DNA-carrier complex were loaded on 11 mL gradients and the tubes were loaded in a SW40 rotor and centrifuged for 2.5 hours at 40,000 rpm and 10° C. Thirty to thirty-two fractions were collected from each gradient after centrifugation. Twenty μL aliquots of each fraction in 1.5 μL loading dye (40% sucrose, 0.25% Bromophenol blue) were run on a 0.8% agarose gel in 89 mM Tris-Borate 2 mM EDTA, pH 8.3 and 0.5 mg/mL ethidium bromide. Gels were run at 80 volts for 2 hours.

Laser Light Scattering Measurments

Light scattering measurements were determined on a Dawn DSP Laser Light Scattering instrument (Wyatt, Santa Barbara, Calif.) in the batch mode. Particle size standards were obtained from Duke Scientific, Palo Alto, Calif.

EXAMPLE 1

Characterization of Carrier Molecules Prepared With Varying Concentrations of Salt and Base In order to determine a sufficient concentration of salt and base for forming disperse, homogeneous carrier molecules, conjugates of asialoorosomucoid (ASOR) and 26 kD poly-L-lysine (Pl) were prepared as described above and the final salt concentration was varied as set forth below in Table 1. The conjugates were then characterized by radius measurements determined on a Dawn DSP Laser Light Scattering instrument in the batch mode.

The results are set forth below in Table 1 and demonstrate that an optimal salt and base concentration for forming carrier molecules is about 1.0 M NaCl or higher and about 2.0 mM NaOH. At these concentrations, the size of the AsOR-Pl carrier becomes appreciably smaller indicating the diminution of self-association and aggregation.

TABLE 1

| Solvent | Radius (nm) | Error (nm) |
|---|---|---|
| Water | 27.8 | 1.8 |
| 0.15 M NaCl | 24.5 | 1.3 |
| 0.30 M NaCl | 24.6 | 0.6 |
| 0.50 M NaCl | 26.5 | 0.7 |
| 0.75 M NaCl | 31.5 | 1.1 |
| 1.00 M NaCl | 31.9 | 0.9 |
| 1.00 M NaCl + 2 mM NaOH | <10 | |

EXAMPLE 2

Characterization Of Polynucleotide-carrier complexes Formed With Disperse vs. Non-Disperse Starting Materials Polynucleotide-carrier complexes containing pCMV/β-galactosidase plasmid DNA linked to an ASOR-Pl conjugate were prepared according to (a) the improved "disperse" method described above and (b) the standard "non-disperse" method (i.e., a step-down salt gradient process), also described above. The size, homogeneity, and level of aggregation of the polynucleotide-carrier complexes were characterized by their appearance agarose gels of sucrose density gradient fractions, prepared as described above.

Figure 1B:
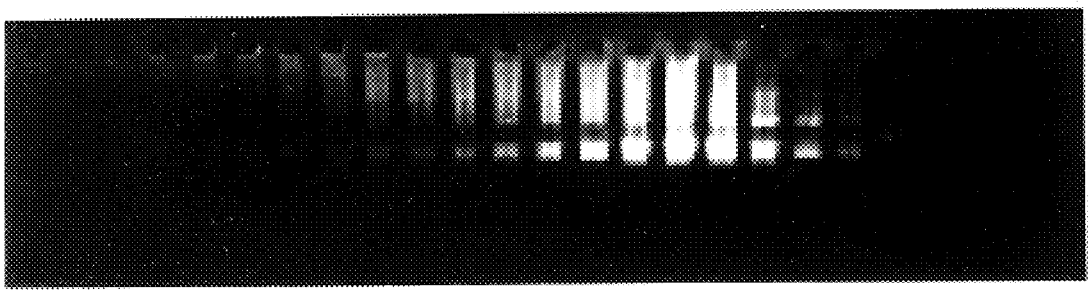

The results are shown in FIG. 1. Panel A shows a gel containing the complex formed by the non-disperse method. Panel B shows a gel containing the complex formed by disperse method of the present invention. As shown in Panel B, the complex formed by the disperse method is highly unaggregated and homogeneous, in contrast to the complex formed by the non-disperse method (Panel A). For example, there are no detectable bands at the bottom of the sucrose gradient (e.g., lanes 1–6), indicating that the complex does not contain any large aggregates and is highly soluble. Further, the conjugate formed by the disperse method appears in a relatively narrow section toward the top of the sucrose gradient (approximately lanes 8–20), demonstrating a substantial level of homogeneity in size.

Overall, these results demonstrate the improved solubility, dispersity and homogeneity of complexes formed by the method of the present invention compared to the standard, non-disperse method.

EXAMPLE 3

In Vivo Expression of Luciferase and β-Galactosidase Using Polynucleotide-carrier complexes or Free Polynucleotide To demonstrate the improved performance of complexes prepared according to the improved method of the present invention (i.e., the "disperse method" described above), as measured by levels of gene expression, a series of in vivo animal studies were performed. The protocols used for these studies are described above in the Materials and Methods Section.

In these studies (described in this and the following Examples), a variety of parameters were systematically varied to demonstrate the broad applicability of the present invention, including the particular ligand, polycation and cDNA plasmid used in the complex. In addition, the effect on expression levels caused by extruding the complex through a 50 nm filter was tested. Still further, the effect on expression levels caused by varying the charge ratio of the complex was tested. The results of all of these various studies are discussed below.

I. Higher Levels of Luciferase Expression in vivo Correlates with Increased Dispersity, Solubility and Homogeneity of Polynucleotide-carrier complexes This study was designed to (1) compare the level of luciferase expression obtained with complexes formed by the improved disperse method verses the standard non-disperse method, and (2) compare the level of luciferase expression obtained using different polycations and ligands in the complex.

Mice were injected in triplicate with free plasmid DNA (pCMV-Luc) or the following complexes formed by either the disperse or non-disperse method (a) pCMV-Luc-protamine-DNA; (b) pCMV-Luc-26 kD polylysine-DNA; (c) pCMV-Luc-26 kD polylysine-BSA[1]; and (d) pCMV-Luc-26 kD polylysine-ASOR. All complexes were prepared at 50% charge neutralization.[2]

[1]BSA was used as a control since it does not bind to any receptor on liver cells and, therefore, would not contribute to delivery of the complex to mouse liver cells. [2] charge neutralization refers to neutralization of negative DNA charge by positive polycation (e.g., polylysine) charge.

The amount of plasmid DNA injected per mouse (either as free DNA or as a complex) was 10 μg delivered by tail vein. The mice were sacrificed at 24 hours and the livers removed and assayed for luciferase activity as described above in the materials and methods section.

As shown in Table 2, free plasmid DNA and each complex formed by the new disperse method exhibits significantly higher expression than does the corresponding free plasmid DNA or complex formed by the standard non-disperse method. In addition, complexes of DNA-protamine, DNA-Pl-BSA and DNA-Pl-ASOR show appreciably higher levels of expression than do the free DNA or DNA-Pl complex.

TABLE 2

| Ligand | Non-Monodisperse Formulation (pg/μg DNA)[1] | Monodisperse Formulation (pg/μg DNA)[1] | Fold-Increase |
|---|---|---|---|
| Free pCMV-Luc | 2242 | 13964 | 6.2 |
| Protamine pCMV-Luc | 13357 | 87037 | 6.5 |
| Polylysine pCMV-Luc | 7848 | 14041 | 1.8 |
| BSA 26K pCMV-Luc | 771 | 38668 | 50.2 |
| AP26K pCMV-Luc | 23753 | 222639 | 9.4 |

[1] Each number represents the average picograms Luciferase expressed in 3 mice sacrificed at 24 hours post-injection. The mice were injected intravenously through the tail vein with 10 μg/ml DNA or DNA complex.

To study the correlation between levels of expression obtained in vivo in mice and the size of the complexes tested, agarose gel analyses of sucrose gradient fractions containing these complexes was performed. The protocol used is described above in the Materials and Methods section. The results are shown in FIGS. 3(a) and 3(b). Aliquots from all regions of the sucrose gradient, ranging from the bottom of the gradient (fraction 1) to the top of the gradient (fraction 30 or 31), were run on the gels.

Figure 2A:
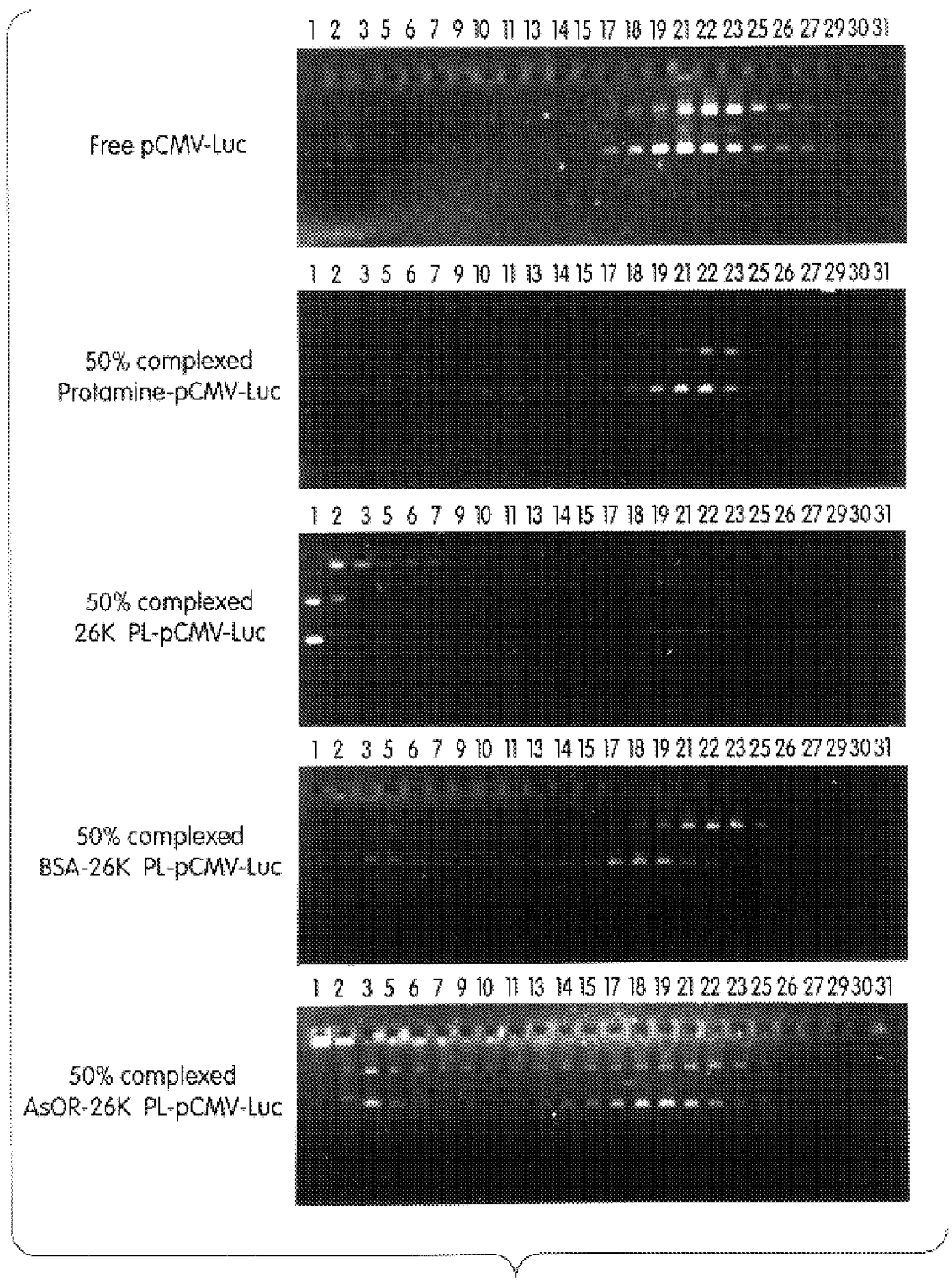
FIGS. 2(a) and 2(b) show a comparison of agarose gels of sucrose density gradient fractions containing the complexes and free plasmid DNA described in FIG. 2 formed by the non-disperse method (FIG. 2(a)) and by the improved disperse method (FIG. 2(b)).
Figure 2B:
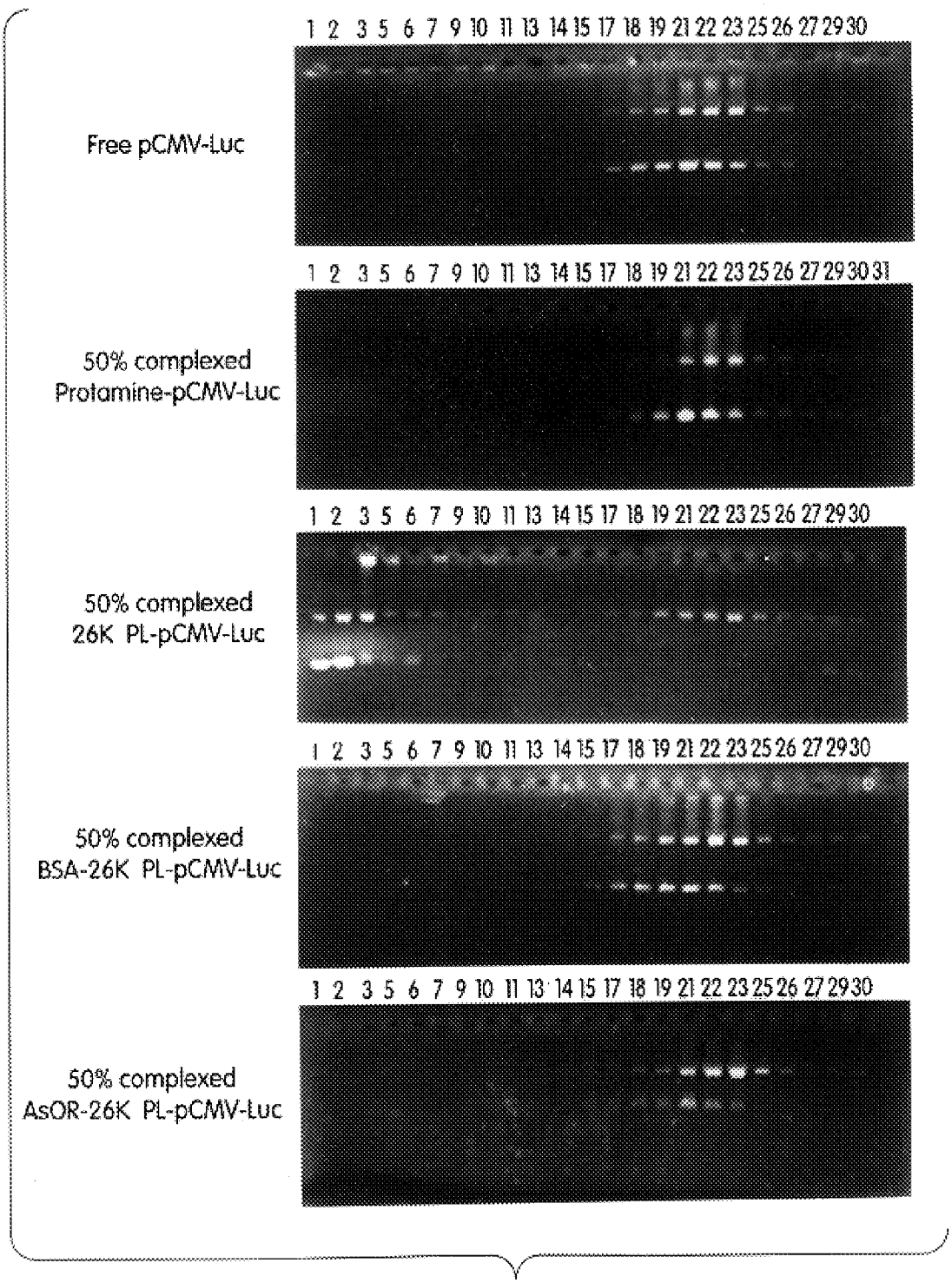

FIG. 2(a) shows gels containing complexes formed by the non-disperse method. FIG. 2(b) shows gels containing complexes formed by the new disperse method of the present invention. A comparison of FIGS. 2(a) and 2(b) shows a discernably higher level of dispersity (i.e., reduced aggregation), solubility, and homogeneity for the complexes formed by the new disperse method, as compared to complexes formed by the standard non-disperse method.

In particular, the complexes containing DNA-protamine, DNA-Pl-BSA and DNA-Pl-ASOR, which exhibit the greatest increase in expression when formed by the new disperse method (compared to the non-disperse method), also show the greatest increase in dispersity, solubility and homogeneity as judged by their performance in sucrose density gradients. For example, the appearance of heavy, less soluble aggregates at the bottom of the sucrose gradient (e.g., fractions 1–8) in FIG. 2(a) disappears in FIG. 2(b) when the complex is formed by the disperse method. In addition, the complexes formed by the disperse method FIG. 2(b) appear in a smaller cross-section of the gradient (approximately fractions 17–26), indicating a more homogenous composition.

Figure 3:
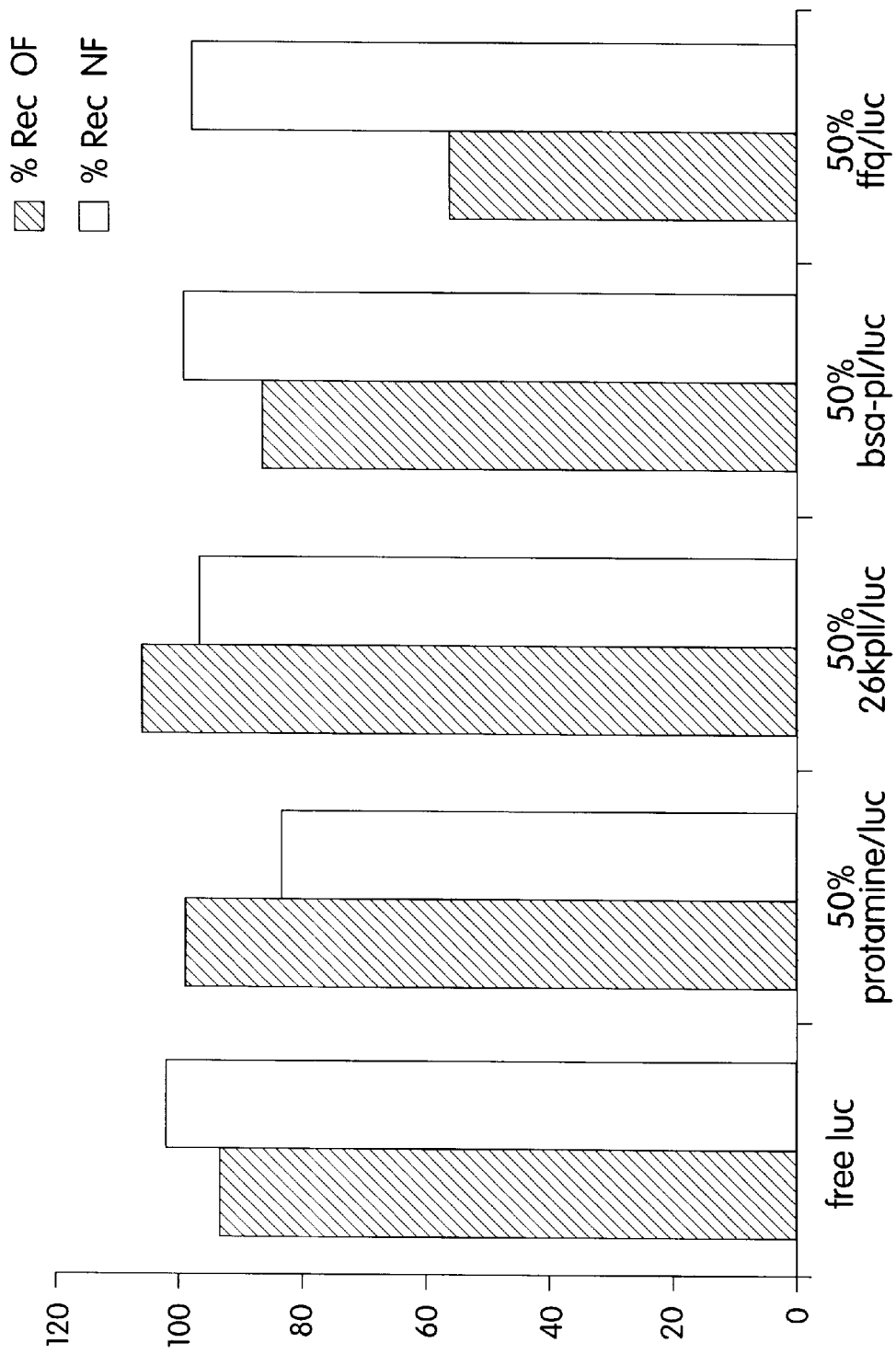
FIG. 3 is a graphic representation showing the percent recovery of the complexes and free plasmid DNA described in FIG. 2 following 0.2μ filtration.

As a final step, all of the complexes and the free plasmid DNA prepared by both the disperse and non-disperse methods were assessed by 0.2μ filtration and recovered as a crude measure of aggregation. The results are shown in FIG. 3 and demonstrate that recovery of free plasmid DNA (free luc) and complexes containing DNA-Pl-BSA (bsa-pl/luc) and DNA-Pl-ASOR (ffq/luc) is improved from 9–41% when these species are formed by the disperse method.

Overall, the results of the studies described above clearly demonstrate that there is a direct correlation between higher levels of gene expression obtained with complexes formed by the disperse method of the present invention and their improved physical characteristics, including increased solubility and homogeneity, and reduced aggregation.

II. Improved β-Galactosidase Expression in vivo Correlates with Increased Dispersity, Solubility and Homogeneity of Complexes This study was identical to the luciferase study described directly above in subsection I, except that a plasmid encoding β-galactosidase, pCMV-β-gal, was used in place of pCMV-Luc in each of the complexes tested and as free DNA.

Accordingly, mice were injected in triplicate with free plasmid DNA or complexes formed by either the non-disperse or the new disperse method. The complexes tested contained (a) pCMV/β-gal-protamine; (b) pCMV/β-gal-26 kD polylysine; (c) pCMV/β-gal26 kD polylysine-BSA; (d) pCMV/β-gal-26 kD polylysine-ASOR or (e) free plasmid DNA (pCMV-β-gal). All complexes were prepared with a 50% DNA charge neutralization ratio.

The amount of plasmid DNA injected per mouse (either as free DNA or as a complex) was 10 μg delivered by tail vein. The complex was injected in a total volume of 1.0 mL. The mice were sacrificed at day 5 post-injection and their livers were removed and assayed for β-gal expression as described above in the Materials and Methods section.

Figure 4:
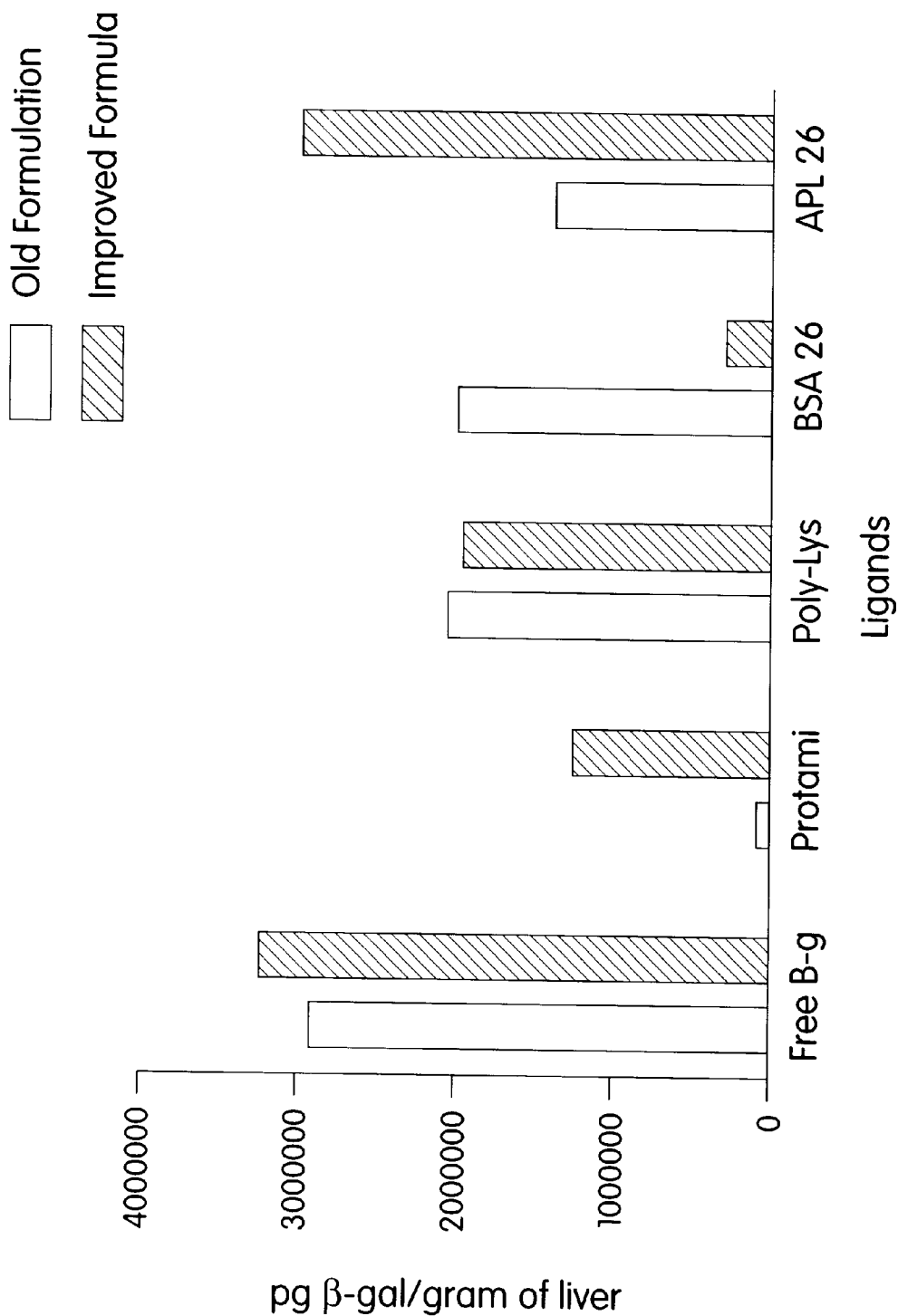
FIG. 4 is a graphic representation comparing expression levels observed in livers of mice 5 days after injection of the following polynucleotide-carrier complexes formed by either the disperse or non-disperse method: (a) pCMV/βgal-protamine; (b) pCMV/βgal-26 kD polylysine; (c) pCMV/βgal-26 kD polylysine-BSA; (d) pCMV/βgal-26 kD polylysine-ASOR or (e) free plasmid DNA (pCMV/βgal). All complexes were prepared at 50% charge neutralization and the total amount of plasmid DNA injected per mouse (either as free DNA or as a complex) was 10 μg.
Figure 5A:
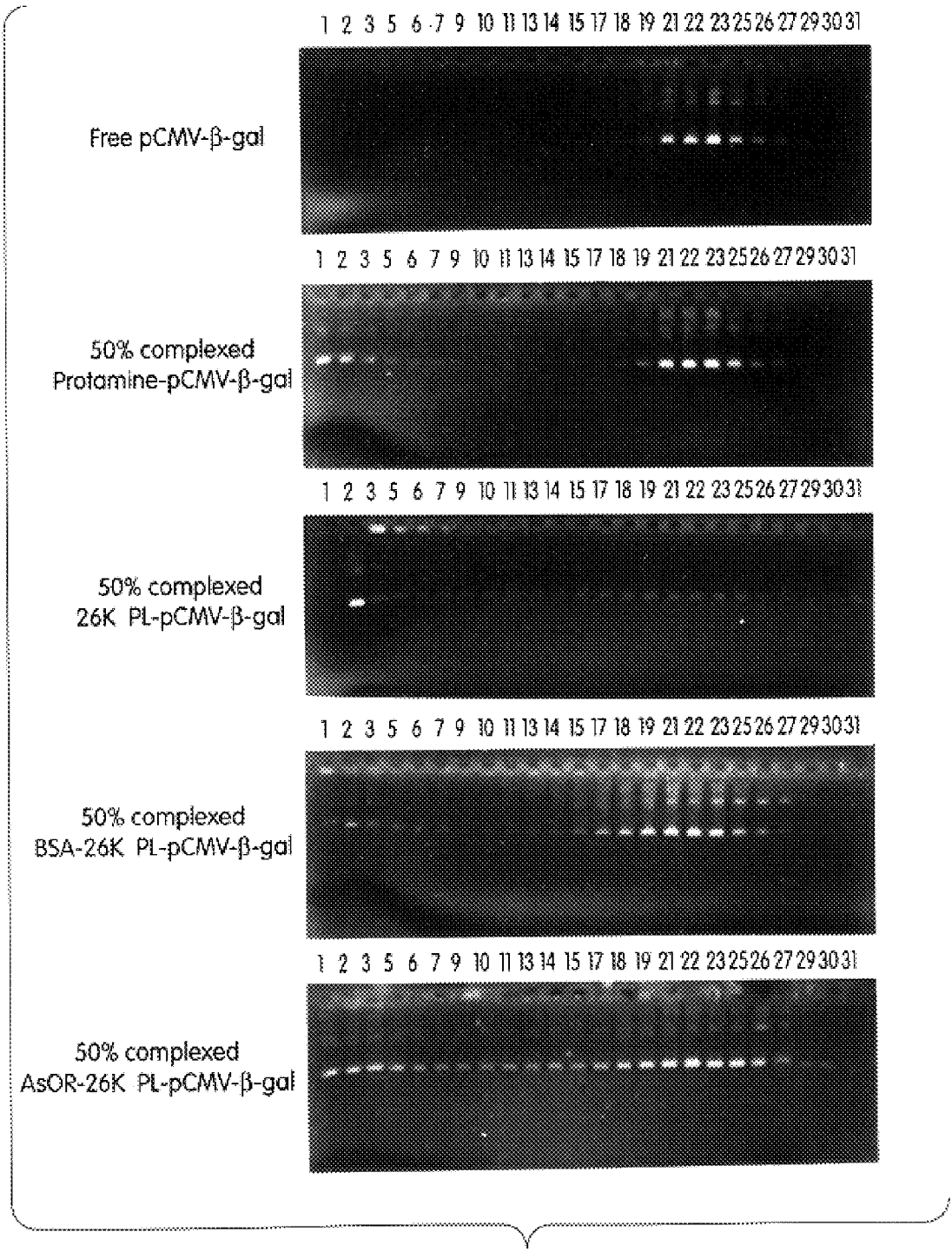
FIGS. 5(a) and 5(b) show a comparison of agarose gels of sucrose density gradient fractions containing the complexes and free plasmid DNA described in FIG. 5 formed by the non-disperse method (FIG. 6(a)) and by the improved disperse method (FIG. 6(b)).
Figure 5B:
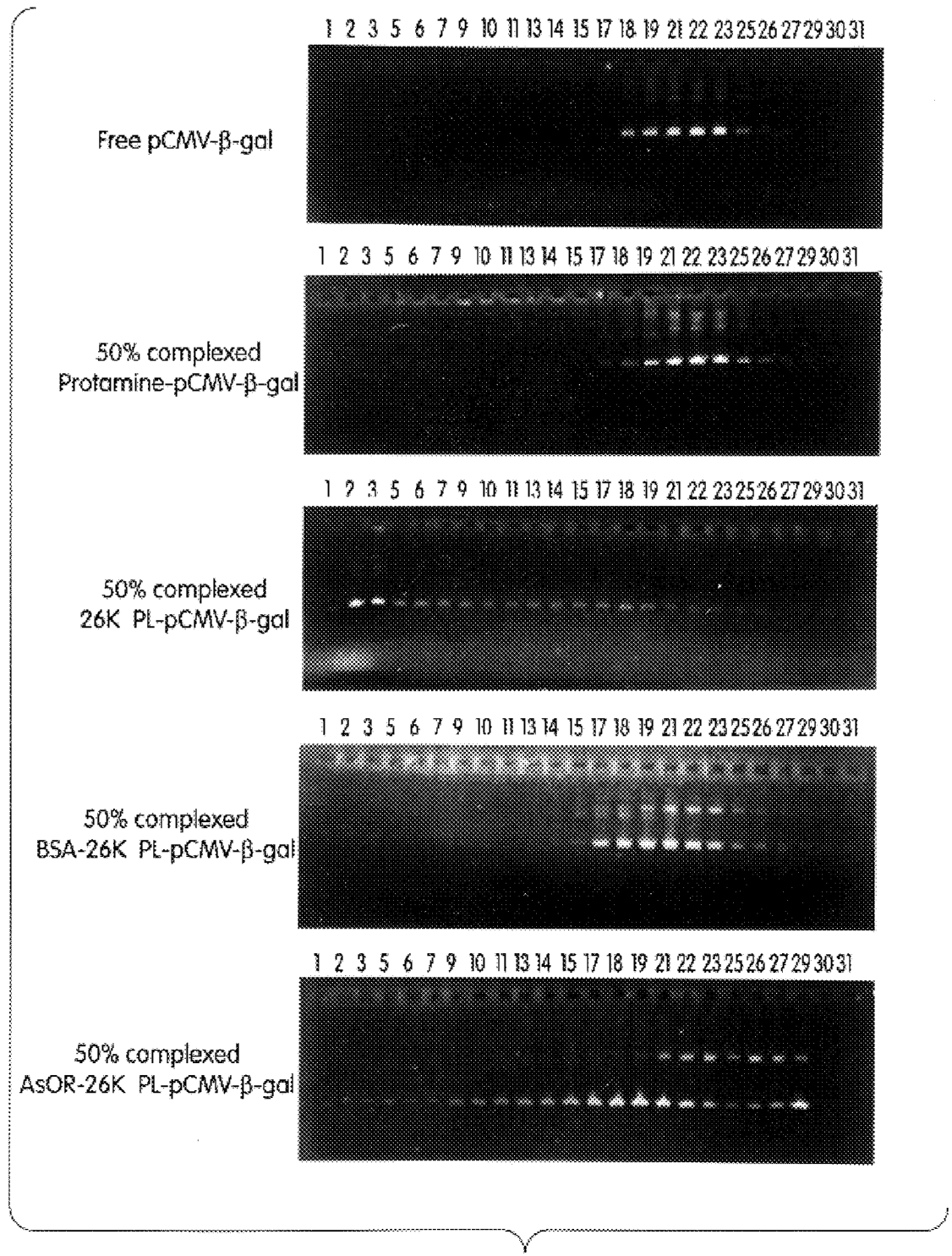
Figure 6:
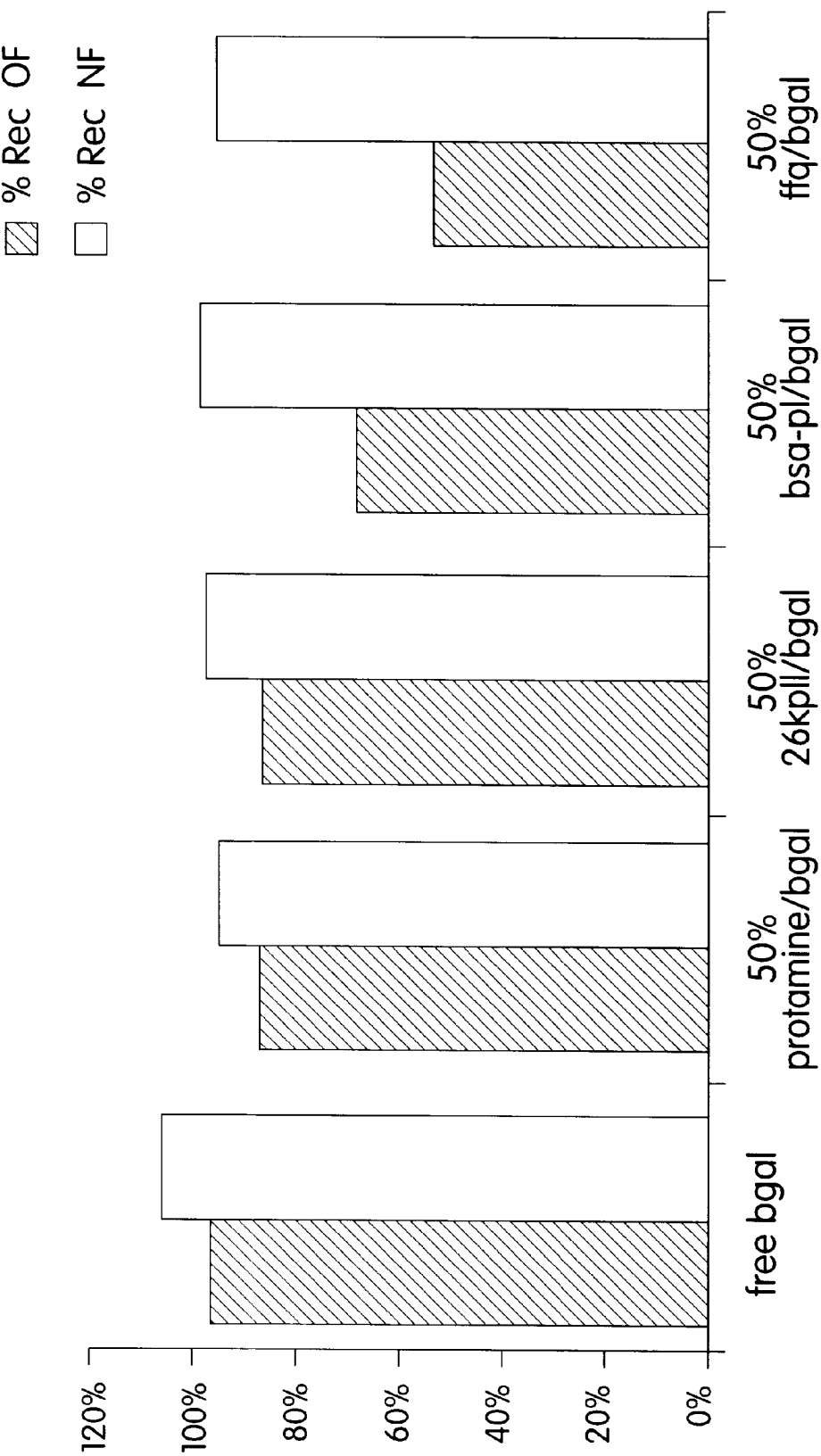
FIG. 6 is a graphic representation showing the percent recovery of the complexes and free plasmid DNA described in FIG. 5 following 0.2μ filtration.

The results are shown in FIG. 4 and demonstrate that free plasmid DNA and complexes containing DNA-protamine or DNA-Pl-ASOR formed by the improved disperse method exhibited significantly higher expression than did the corresponding free plasmid DNA or complexes formed by the standard non-disperse method. In addition, when analyzed by sucrose density gradient gels (FIGS. 5(a) and 5(b)), the increased expression of these complexes correlated with a marked improvement in their level of solubility and homogeneity, showing substantially less aggregation. This was further confirmed by an increase from 7–40% in the percent recovery following 0.2μ filtration of all complexes tested (as well as the free DNA) (FIG. 6).

Overall, the results of the β-galactosidase complex studies described above again demonstrate a correlation between improved levels of gene expression obtained with complexes formed by the disperse method of the present invention and improved physical characteristics of these complexes, including increased solubility and homogeneity, and educed aggregation.

EXAMPLE 4

Effect of Net Charge of Polynucleotide-carrier Complexes on Gene Expression

To study the effect on expression levels caused by variation of the net global charge of polynucleotide-carrier complexes (i.e., the percent of neutralization of the negatively charged DNA by the positively charged polycation) formed by the improved, disperse method, pCMV/Luc-Pl-ASOR complexes were prepared with charge neutralization ratios (cationic carrier: anionic DNA) of 100%, 200%, 500% or 1000%. A complex of pCMV/Luc and free polylysine (pCMV/Luc-Pl) having a 1000% charge neutralization ratio was used as a control. Mice were injected in triplicate with complex via tail vein and sacrificed at day 5 post injection. Livers were removed and assayed for luciferase activity according to the protocols described above.

As shown in FIG. 7, strongly cationic (e.g., 200%, 500% and 1000% neutralized) DNA-Pl-ASOR complexes achieve higher levels of expression than do more neutral (e.g., 100%) DNA-Pl-ASOR complexes which have a proportionately larger hydrophobic component. In addition, 1000% neutralized DNA-Pl-ASOR complexes achieve higher expression than do 1000% neutralized DNA-Pl complexes.

Overall, these results clearly show that, while a more net positive charge generally increases expression levels of a given complex, other variables are also involved, such as the solvation characteristics of the complex. This is indicated by the fact that 1000% neutralized DNA-Pl complexes exhibit lower expression than do 1000% neutralized DNA-Pl-ASOR complexes. It is likely that the hydrophobic nature of the unconjugated polylysine is detrimental to the overall performance of the complex.

EXAMPLE 5

Extrusion Enhances Performance of Polynucleotide Complexes as Measured by Gene Expression To study the effect of extrusion on performance of gene complexes formed by the disperse method of the present invention, a comparison was made of the expression obtained with two different complexes, pCMV/Luc-Pl-ASOR (100% charge neutralization) and pCMV/hGH-Pl-ASOR (50%,100%, 250% and 500% charge neutralization),[3] with and without extrusion of complexes through a 50 nm filter prior to injection into mice. The results from each gene plasmid complex are described separately below.

I. pCMV/Luc-Pl-ASOR (100% charge neutralization)

To test the effect of extrusion on 100% neutralized pCMV/Luc-Pl-ASOR complexes, one set of mice was injected via tail vein with the extruded complex. Another set of mice was similarly injected with the non-extruded complex. Livers were then assayed for luciferase expression at day 4. Both sets of animals were treated prior to administration with colchicine both intraperitoneally and orally.

Figure 8:
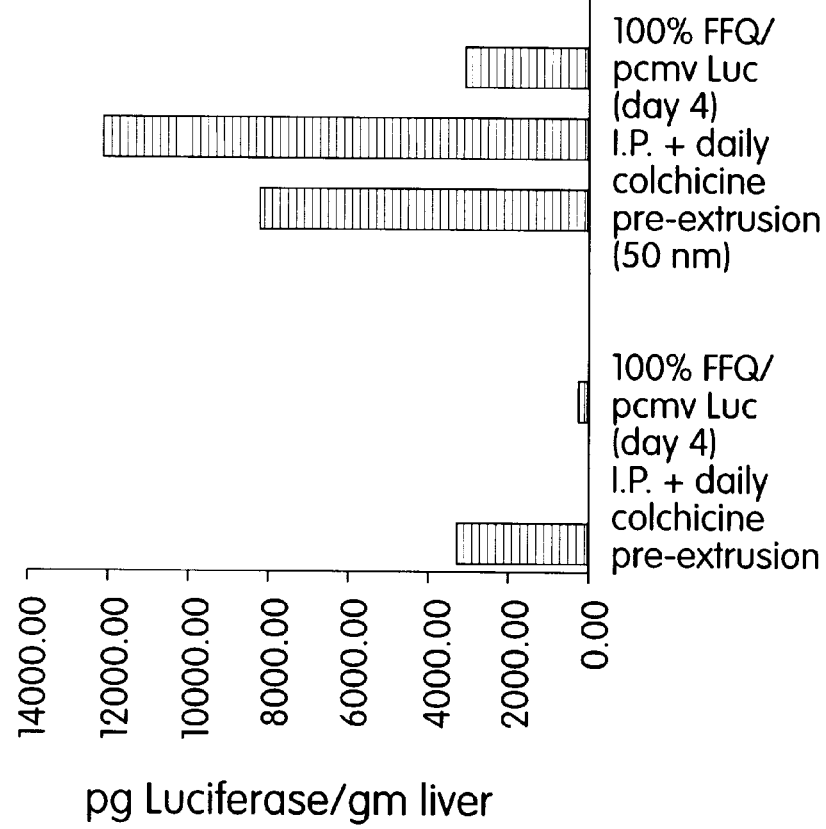
FIG. 8 is a graphic representation comparing the levels of luciferase expression obtained from 100% neutralized pCMV/Luc-Pl-ASOR complexes pre-extrusion and post-extrusion through a 50 nm filter. Mice were treated daily with colchicine, both intraperitoneally and orally. Livers were then assayed for luciferase expression at day 4.

As shown in FIG. 8, the extruded sample exhibited far higher expression than did the unextruded sample. This demonstrates that suboptimal performance of a given complex (due perhaps to hydrophobic interactions) can be improved by taking additional steps that diminish aggregation prior to administering the complex in vivo, such as extruding the complex.

To study the correlation between the improved performance (e.g., expression) of extruded DNA-Pl-ASOR complexes and their physical characteristics, laser light scattering (LLS) radius measurements were taken of the complexes prepared with and without extrusion. The results are shown below in Table 3. While the samples measured by LLS were not the same samples used in the above expression study, the measurements taken clearly show that extruded complexes are more homogenous and smaller in size than unextruded complexes. In each determination, the extruded complex was determined to be smaller than the nonextruded material.

TABLE 3

| BEFORE EXTRUSION | | AFTER EXTRUSION | |
|---|---|---|---|
| RMS Radius (nm) | Error (nm) | RMS radius (nm) | Error (nm) |
| 89.4 | 1.5 | 59.6 | — |
| 104.3 | 4.5 | 54.0 | — |

TABLE 3-continued

| BEFORE EXTRUSION | | AFTER EXTRUSION | |
|---|---|---|---|
| RMS Radius (nm) | Error (nm) | RMS radius (nm) | Error (nm) |
| 85.0 | 14.3 | 51.8 | — |
| 53.8 | 1.9 | 44.2 | 0.6 |
| 74.7 | 1.8 | 51.9 | 0.9 |
| 77.7 | 5.3 | 52.7 | 2.8 |
| 75.3 | 1.3 | 54.5 | 0.3 |
| 94.5 | 3.1 | 54.0 | 1.8 |
| 84.0 | 10.4 | 52.3 | 6.0 |

II. pCMV/hGH-Pl-ASOR (100%, 250% and 500% charge neutralization)

A second study, similar to that performed with the pCMV/Luc-Pl-ASOR complex, was conducted for pCMV/hGH-Pl-ASOR complexes having varying degrees of charge neutralization (50%, 100%, 250% and 500%). One set of these complexes was injected directly into mice, each mouse receiving a total of 10 μg of DNA. Another set of these complexes was extruded through a 50 nm filter prior to being injected into mice. Mice which were injected with the extruded complexes received a total of 10 μg of DNA for the 50% neutralized complex, 8 μg of DNA for the 100% neutralized complex, and 4 μg of DNA for the 250% and 500% neutralized complexes.

Mice were sacrificed at day 3, 7 and 14 post-injection and their livers were assayed for hGH expression. As shown in Table 4 below, the extruded complexes all exhibited higher levels of expression (e.g., up to an 18.2 fold-increase[4]) over the corresponding unextruded complexes. This increase was overall the highest for the 250% neutralized complex which, even at day 14, exhibited a 12.7 fold-increase in expression over the corresponding unextruded complex.

[4] fold-increase values are corrected for variation in amounts of plasmid DNA injected into mice for the extruded complexes.

TABLE 4

| Post-Injection | AP 26K-pCMVhGH % Neutralization | Average ng/ml Pre-extrusion | Average ng/ml[1] Post-extrusion | Fold-Increase |
|---|---|---|---|---|
| Day 3 | 50% | 1.9 | 34.6 | 18.2 |
| | 100% | 2.2 | 4.9 | 2.2 |
| | 250% | 0.7[2] (2.3) | 12.3 | 17.6 (5.3) |
| | 500% | 0.9[2] | 1.5 | 1.7 |
| Day 7 | 50% | 1.6 | 13.8 | 8.6 |
| | 100% | 1.7 | 4.3 | 2.5 |
| | 250% | 0.9[2] (0.8) | 11.8 | 13.1 (14.8) |
| | 500% | 0.5[3] (2.3)[2] | 1.5[2] | 3.0 (0.7) |
| Day 14 | 50% | 1.0[2] | 9.2 | 9.2 |
| | 100% | 0.5 | 3.4 | 6.8 |
| | 250% | 0.6 | 7.6 | 12.7 |
| | 500% | 0.3[3] (0.2)[2] | 0.6[2] | 2.0 (3.0) |

[1]The averages have been corrected for the amount of DNA injected.
[2]Average of two mice due to bad injection, death of mouse or spurious data. In the case of spurious data the average including the suspect data is given in parentheses.
[3]Data based on one mouse.

To study the correlation between the increase in expression observed for the extruded complexes and a change in their physical characteristics, sucrose density gel analysis was performed on each complex as previously described. As shown in FIGS. 10(*a*) and 10(*b*), there is a marked improvement in the level of dispersity (i.e., reduced aggregation), solubility and homogeneity for each of the complexes following extrusion. This can be seen by an overall reduction in the number of bands on the gels, as in FIG. 10(a) (50% and 100% neutralized complexes), indicating a more homogenous composition. This can also be seen by a disappearance of bands near the bottom of the gels, as in FIG. 10(b) (250% and 500% neutralized complexes), indicating an absence of aggregates, for each of the extruded complexes.

Overall, the results of the studies described above show that additional measures, such as extrusion, which diminish aggregation of complexes and improve their dispersity and homogeneity, can improve the performance (e.g., level of gene expression) of a variety complexes (e.g., containing different polynucleotides and having different charge ratios) formed by the improved disperse method of the present invention. Such measures may include, in addition to extrusion, temperature variations, pH changes and measures which diminish inhibitory actions which occur in vivo (e.g., opsonization of the complex by inhibitory factors present in blood serum).

EXAMPLE 6

Complexes Rapidly Reach Target Cells in a Receptor-Specific Manner

To demonstrate that complexes prepared by the disperse method of the present invention are rapidly internalized by target cells in vivo in a receptor-specific manner, biodistribution studies were performed in mice using Iodine-125 radiolabeled CMV/pLuc-Pl-ASOR complexes. One set of animals (Group 1) was injected via tail vein with radiolabeled complex. A second set of animals (Group 2) received both complex and 2 mg of free ASOR in the same injection. A third set of animals (Group 3) received both complex and 2 mg of dextran in the same injection. Animals were tested in sets of three.

Figure 9:
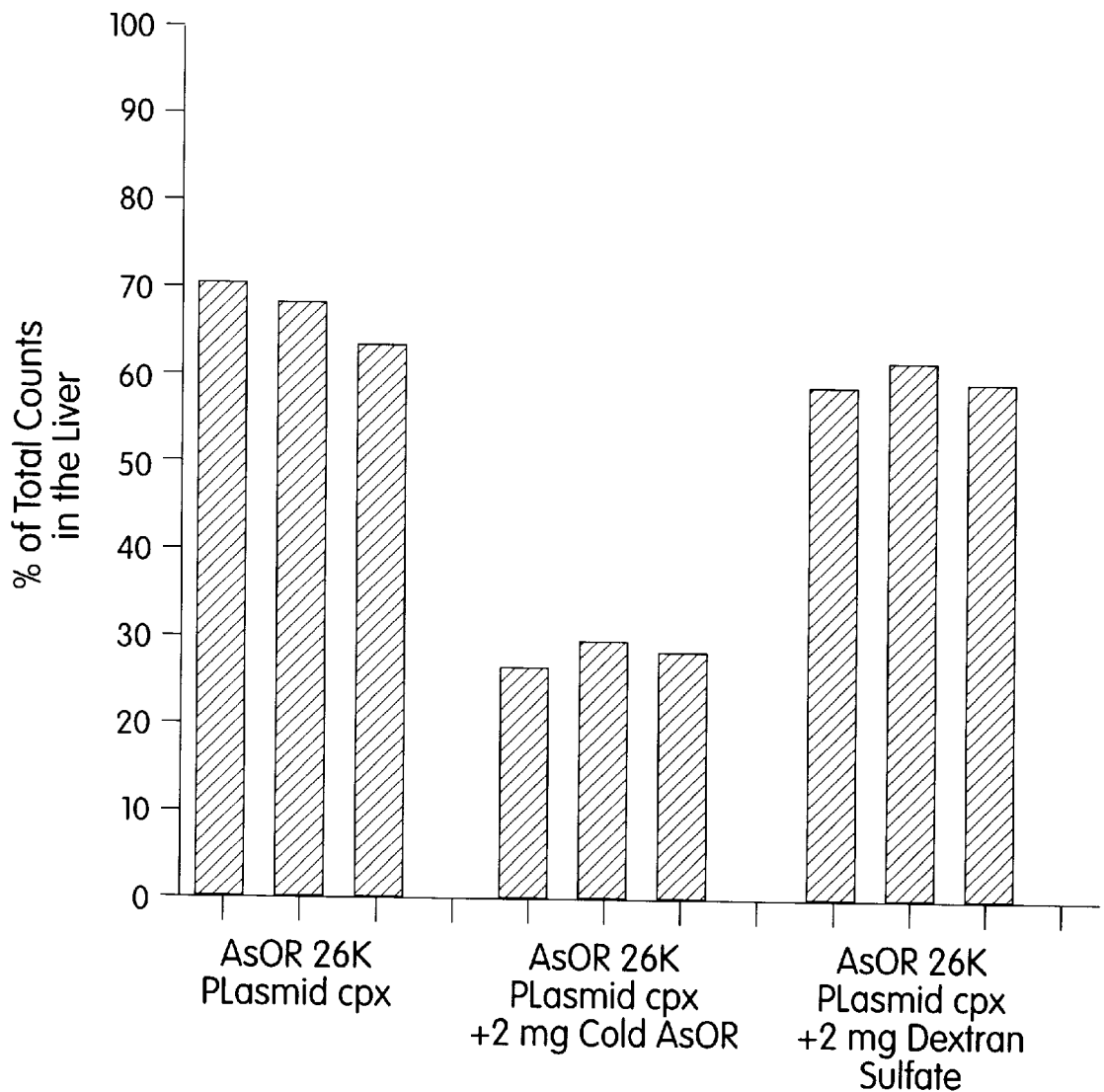
FIG. 9 is graphic representation comparing the total amount of Iodine-125 radiolabeled CMV/pLuc-Pl-ASOR complex which reaches the liver in (a) mice injected with complex alone, (b) complex and 2 mg of free (cold) ASOR, and (c) complex and 2 mg of dextran.

As shown in Table 5, Group 1 had 67.36+/−3.73% of the injected dose in the liver after only 5 minutes of circulation. Only very small percentages of the injected dose were detectable in the other organs (i.e., spleen, kidney, heart, lung and blood). However, the amount of complex targeted to the hepatic compartment in Group 2 was reduced to 28.14+/−1.81, a decrease of 58% from Group 1. This demonstrates that competition with free ASOR reduces the amount of complex which reaches liver cells.[5] In addition, in Group 3, which received a coinjection of dextran sulfate (an agent known to block Kupffer cell uptake), hepatic uptake of complexes decreased to 59.91+/−1.28% of the injected dose. A graphic representation comparing the overall amount of complex which reached the liver in each of the three groups tested is shown in FIG. 9.

[5] A concomitant rise in the blood values raised the amounts detected in all other organs marginally.

Overall, the results of the three groups taken together indicate that the pCMV-Pl-ASOR complex is targeted in a receptor specific manner to liver cells, since it can be competed by excess specific ligand (ASOR). In addition, blocking Kupffer cells with dextran sulfate decreased hepatic targeting by only 11% indicating that the great majority of the targeting is to parenchymal cells containing asialoglycoprotein receptor (ASGr) specific for ASOR.

TABLE 5

| Sample | No Competition % Total Counts[1] GROUP 1 | Competed with ASOR % Total Counts[1] GROUP 2 | Competed with Dextran Sulfate % Total Counts[1] GROUP 3 |
| --- | --- | --- | --- |
| Liver | 67.4 ± 3.7 | 28.1 ± 1.8 | 59.9 ± 1.3 |
| Spleen | 0.4 ± 0.1 | 1.1 ± 0.1 | 0.3 ± 0.1 |
| Kidney | 2.5 ± 0.1 | 13.1 ± 0.6 | 1.4 ± 0.2 |
| Heart | 0.3 ± 0.1 | 1.7 ± 1.7 | 0.3 ± 0.1 |
| Lung | 1.0 ± 0.3 | 2.7 ± 0.9 | 1.3 ± 0.4 |
| Total Blood | 5.4 ± 0.8 | 28.7 ± 3.6 | 11.8 ± 2.7 |
| Total Organs | 71.6 ± 3.9 | 45.7 ± 2.7 | 63.3 ± 0.8 |

[1]Average of 3 mice.

EXAMPLE 7

Complexes Can Be Prepared Using A Variety of Polycations

This study was designed to show that a variety of polycations, other than 26 kD polylysine, can be used in complexes formed by the improved, disperse method of the present invention to achieve high levels and duration of expression at a variety of charge neutralization levels.

A series of complexes were prepared according to the disperse method, as described above in the Materials and Methods section, using pCMV/hGH and a carrier molecule made up of 4 kD polylysine (4 kD Pl) and ASOR. These complexes had varying degrees of charge neutralization corresponding to 0% (free plasmid DNA), 89%, 178%, 356% and 890%. The complexes were injected into mice and assayed for expression at day 2, 7 and 14 post-injection.

Figure 11:
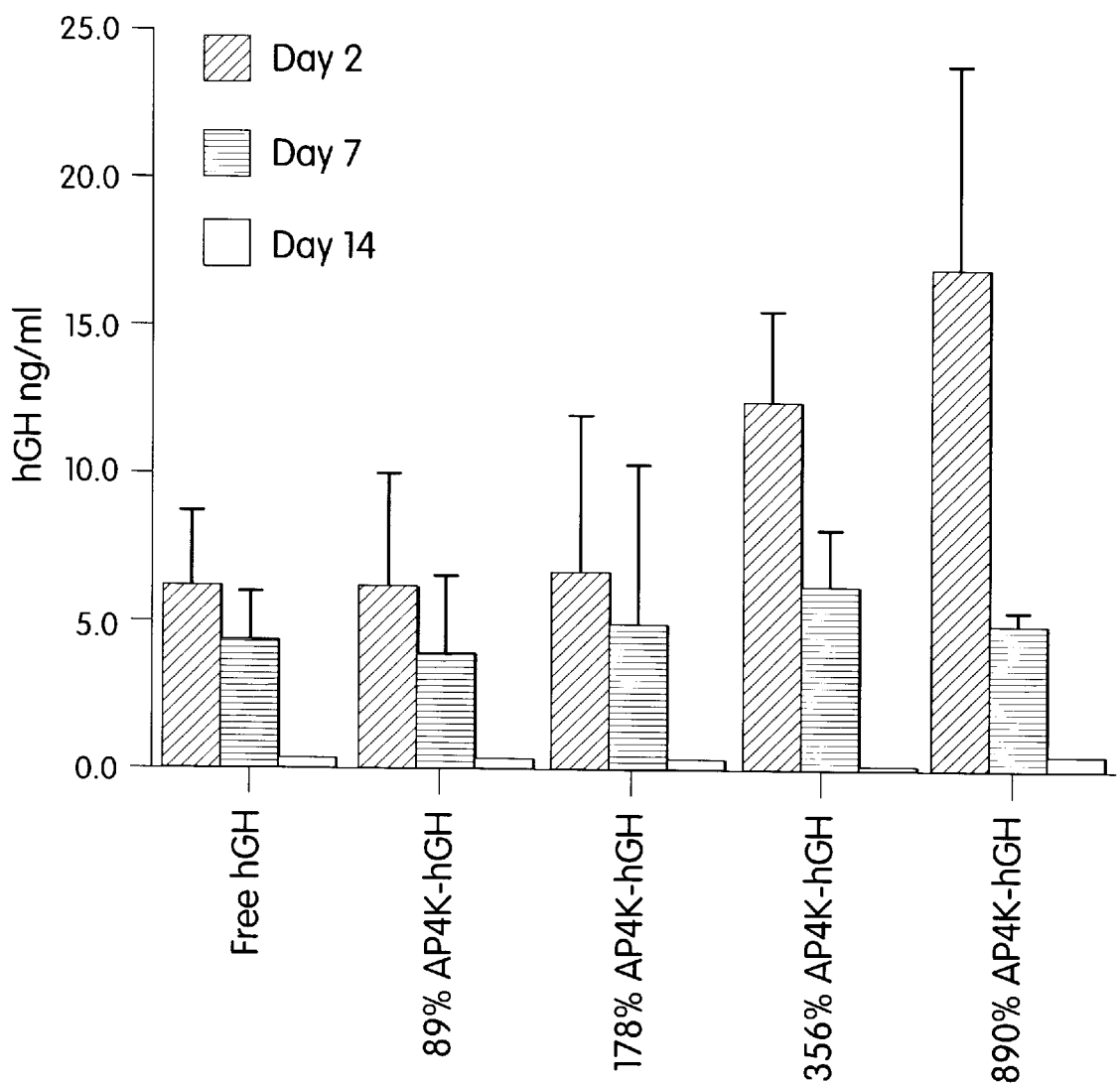
FIG. 11 is a graphic representation of the levels of hGH expression obtained from complexes prepared by the improved disperse method which contain pCMV/hGH and a carrier made up of 4 kD polylysine and ASOR. The complexes had varying percentages of charge neutralization (89%, 178%, 356%, 890%).

As shown in FIG. 11, high levels of hGH expression were obtained with all complexes. Expression levels were greatest for the more cationic complexes (i.e., the 356% and 890% neutralized pCMV/hGH-Pl(4kD)-ASOR complexes). In addition, on sucrose density gradient gels, these complexes each ran as non-aggregated, homogeneous bands near the top of the gradient (FIG. 12).

Overall, this study indicates that a variety of polycations can be used in the improved method of the present invention to form disperse, homogenous polynucleotide-carrier complexes which exhibit high levels and duration of expression.

EQUIVALENTS

Although the invention has been described with reference to its preferred embodiments, other embodiments can achieve the same results. Those skilled in the art will recognize or be able to ascertain using no more than routine experimentation, numerous equivalents to the specific embodiments described herein. Such equivalents are considered to be within the scope of this invention and are encompassed by the following claims.

What is claimed is:

1. A method of forming a composition of polynucleotide-carrier complexes comprising:
   (a) preparing a carrier solution comprising cationic carrier molecules, a charge shielding agent in an amount sufficient to inhibit aggregation of the carrier molecules, and a charge neutralizing agent in an amount sufficient to neutralize a portion of the positive charge of the carrier; and
   (b) combining the carrier solution with a polynucleotide, thereby forming a solution of polynucleotide-cerrier complexes.

2. The method of claim 1 wherein the charge neutralizing agent is a base.

3. The method of claim 2 wherein the base is selected from the group consisting of sodium hydroxide (NaOH), potassium hydroxide (KOH), ammonium hydroxide (NH$_4$OH), alkylamines, alkoxides and triethanolamines.

4. The method of claim 3 wherein the base is sodium hydroxide (NaOH).

5. The method of claim 4 wherein the concentration of base in the carrier solution is about 10–1000 mM.

6. The method of claim 5 wherein the concentration of carrier molecules in the carrier solution is about 0.5 mg/mL–20.0 mg/mL.

7. The method of claim 1 wherein the solution of polynucleotide-carrier complexes has a final concentration of charge shielding agent and charge neutralizing agent which does not damage or substantially inhibit the function of the polynucleotide.

8. The method of claim 7 wherein the charge shielding agent is a salt and the charge neutralizing agent is a base.

9. The method of claim 8 wherein the final salt concentration is about 0.15–0.5 M and the final base concentration is about 1.0–4.0 mM.

10. The method of claim 9 wherein the final salt concentration is about 0.3 M and the final base concentration is about 2.0 mM.

11. A method of forming a composition of polynucleotide-carrier complexes comprising:

(a) preparing a carrier solution comprising cationic carrier molecules, a salt in an amount sufficient to inhibit aggregation of the carrier molecules, and a base in an amount sufficient to neutralize a portion of the positive charge of the carrier; and (b) combining the carrier solution with a polynucleotide at a final salt concentration which does not damage or substantially inhibit the function of the polynucleotide, thereby foaming a solution of polynucleotide-carrier complexes.

12. The method of claim 11 wherein the portion is about 5–20%.

13. The method of claim 11 wherein the carrier solution has a concentration of carrier molecules of about 3.0–7.0 mg/mL, a concentration of base of about 10–100 mM, and a concentration of salt of about 1.0–5.0 M, and wherein the solution of polynucleotide-carrier complexes has a final concentration of base of about 1.0–4.0 mM and a final concentration of salt of about 0.15–0.5 M.

14. The method of claim 13 wherein the solution of polynucleotide-carrier complexes has a final concentration of base and salt of about 2.0 mM and about 0.3 M, respectively.

15. The method of claim 13 wherein the base is sodium hydroxide (NaOH).

16. A method of forming a composition of polynucleotide-carrier complexes comprising:

(a) preparing a carrier solution comprising cationic carrier molecules at a concentration of about 3.0–7.0 mg/mL, a salt at a concentration of about 1.0–5.0 M, and a base at a concentration of about 10–100 mM; and (b) combining the carrier solution with a polynucleotide at a final salt concentration of about 0. 15–5.0 M and a final base concentration of about 1.0–4.0 mM, thereby forming a solution of polynucleotide-carrier complexes.

17. The method of claim 16 wherein the salt is sodium chloride (NaCl) and the base is sodium hydroxide (NaOH).

18. The method of claim 17 wherein the carrier solution has a carrier molecule concentration of about 5.6 mg/mL, a salt concentration of about 4.7 M, and a base concentration of about 59 mM, and wherein the solution of polynucleotide-carrier complexes has a final salt concentration of about 0.3 M, and a final base concentration of about 2.0 mM.

19. The method of claim 16 further comprising the step of extruding the complex and recovering the extruded product.

20. A method of forming a composition of carrier molecules comprising preparing a solution comprising cationic carrier molecules, a salt at a concentration of about 1.0 M or more, and a base in an amount sufficient to neutralize a portion of the positive charge of the cationic carrier molecules.

21. A solution of carrier molecules for forming polynucleotide-carriage complexes, the solution comprising cationic carrier molecules, a charge shielding agent at a concentration of about 1.0 M or more, and a charge neutralizing agent in an amount sufficient to neutralize a portion of the positive charge of the carrier molecules.

22. The solution of claim 21 wherein the charge neutralizing agent is a base.

23. The solution of claim 22 wherein the cationic carrier molecules are at a concentration of about 0.5–20 mg/mL, wherein the charge shielding agent is a salt at a concentration of about 1.0–10 M, and wherein the charge neutralizing agent is a base at a concentration of about 10–1000 mM.

24. The solution of claim 23 wherein the cationic carrier molecules are at a concentration of about 3.0–7.0 mg/mL, wherein the salt is at a concentration of about 1.0–5.0 M, and wherein the base is at a concentration of about 10–100 mM.

25. The solution of claim 24 wherein the cationic carrier molecules are at a concentration of about 5.0–6.0 mg/mL, wherein the salt is at a concentration of about 4.0–5.0 M, and wherein the base is at a concentration of about 50–70 mM.

26. A solution comprising substantially unaggregated polynucleotide-carrier complexes, a charge shielding agent at a concentration of about 0.5 M or less, and a charge neutralizing agent at a concentration of about 10 mM or less.

27. The solution of claim 26 wherein the charge shielding agent is a salt at a concentration of about 0.15–0.5 M and the charge neutralizing agent is a base at a concentration of about 1.0–4.0 mM.

28. The solution of claim 27 wherein the polynucleotide complexes have been extruded.

* * * * *

UNITED STATES PATENT AND TRADEMARK OFFICE
CERTIFICATE OF CORRECTION

PATENT NO. : 5,994,316
DATED : November 30, 1999
INVENTOR(S) : Lollo et al.

It is certified that error appears in the above-indentified patent and that said Letters Patent is hereby corrected as shown below:

At column 24, line 64, delete "cerrier" and insert --carrier--.

At column 25, line 35, delete "foaming" and insert --forming--.

At column 26, line 4, delete "0. 15" and insert --0.15--.

At column 26, line 25, delete "carriage" and insert --carrier--.

Signed and Sealed this

Fourth Day of July, 2000

Attest:

Q. TODD DICKINSON

*Attesting Officer*      *Director of Patents and Trademarks*